(12) United States Patent
Tai et al.

(10) Patent No.: US 9,733,235 B2
(45) Date of Patent: Aug. 15, 2017

(54) METHODS AND DESIGN OF MEMBRANE FILTERS

(75) Inventors: Yu-Chong Tai, Pasadena, CA (US); Bo Lu, Pasadena, CA (US)

(73) Assignee: CALIFORNIA INSTUTE OF TECHNOLOGY, Pasadena, CA (US)

( * ) Notice: Subject to any disclaimer, the term of this patent is extended or adjusted under 35 U.S.C. 154(b) by 593 days.

(21) Appl. No.: 13/118,332

(22) Filed: May 27, 2011

(65) Prior Publication Data

US 2012/0178097 A1 Jul. 12, 2012

Related U.S. Application Data

(63) Continuation-in-part of application No. 13/078,870, filed on Apr. 1, 2011, now abandoned.

(60) Provisional application No. 61/349,554, filed on May 28, 2010.

(51) Int. Cl.
| | |
|---|---|
| *C12N 5/071* | (2010.01) |
| *G01N 33/50* | (2006.01) |
| *B01D 63/08* | (2006.01) |
| *B01D 65/10* | (2006.01) |
| *B01D 67/00* | (2006.01) |
| *C12M 1/00* | (2006.01) |

(52) U.S. Cl.
CPC ....... *G01N 33/5011* (2013.01); *B01D 63/087* (2013.01); *B01D 65/10* (2013.01); *B01D 67/0034* (2013.01); *B01D 2325/021* (2013.01); *C12M 47/04* (2013.01)

(58) Field of Classification Search
CPC B01D 2325/021; B01D 63/087; B01D 65/10; B01D 67/0034; C12M 47/04; G01N 33/5011
See application file for complete search history.

(56) References Cited

U.S. PATENT DOCUMENTS

| | | | |
|---|---|---|---|
| 6,177,019 B1 * | 1/2001 | Castino et al. | 210/767 |
| 6,177,819 B1 * | 1/2001 | Nguyen | H03K 17/04206 326/27 |
| 6,598,750 B2 * | 7/2003 | Tai et al. | 210/490 |
| 7,846,393 B2 | 12/2010 | Tai et al. | |
| 7,846,743 B2 | 12/2010 | Tai | |
| 8,288,170 B2 | 10/2012 | Tai et al. | |
| 2004/0142463 A1 * | 7/2004 | Walker | A61M 1/36 435/325 |
| 2006/0254972 A1 | 11/2006 | Tai et al. | |
| 2007/0025883 A1 * | 2/2007 | Tai | B01D 61/14 422/400 |
| 2009/0188864 A1 | 7/2009 | Zheng et al. | |
| 2011/0053152 A1 | 3/2011 | Goldkorn et al. | |
| 2011/0217729 A1 * | 9/2011 | Hong | C12M 1/34 435/34 |
| 2013/0143326 A1 | 6/2013 | Tai et al. | |

FOREIGN PATENT DOCUMENTS

| | | |
|---|---|---|
| JP | 5086241 B2 | 9/2012 |
| WO | 2011/150358 A2 | 12/2011 |

OTHER PUBLICATIONS

Kahn (2004) Breast Cancer Research & Treatment 86:237-47.*
Lu et al., "Parylene Membrane Slot Filter for the Capture, Analysis and Culture of Viable Circulating Tumor Cells," MEMS 2010, 23$^{rd}$ IEEE International Conference on Jan. 2010, pp. 935-938.
Zheng et al., "Membrane microfilter device for selective capture, electrolysis and genomic analysis of human circulating tumor cells," Journal of Chromatography A, 2007, vol. 1162, No. 2, pp. 154-161.
International Search Report and Written Opinion, date of mailing Feb. 21, 2012, PCT Application No. PCT/US2010/038390, 13 pages.

* cited by examiner

*Primary Examiner* — Lisa J Hobbs
(74) *Attorney, Agent, or Firm* — Kilpatrick Townsend & Stockton LLP

(57) ABSTRACT

The present invention provides methods for designing a filtration systems for capturing viable tumor cells, such as circulating tumor cells at high efficiency and high viability. The methods involve development of a set of "key engineering design parameters" that are crucial to achieve high tumor cell viability. These important design parameters include the filter geometry design, fluid delivery method, transfilter pressure and total filtration time.

18 Claims, 13 Drawing Sheets

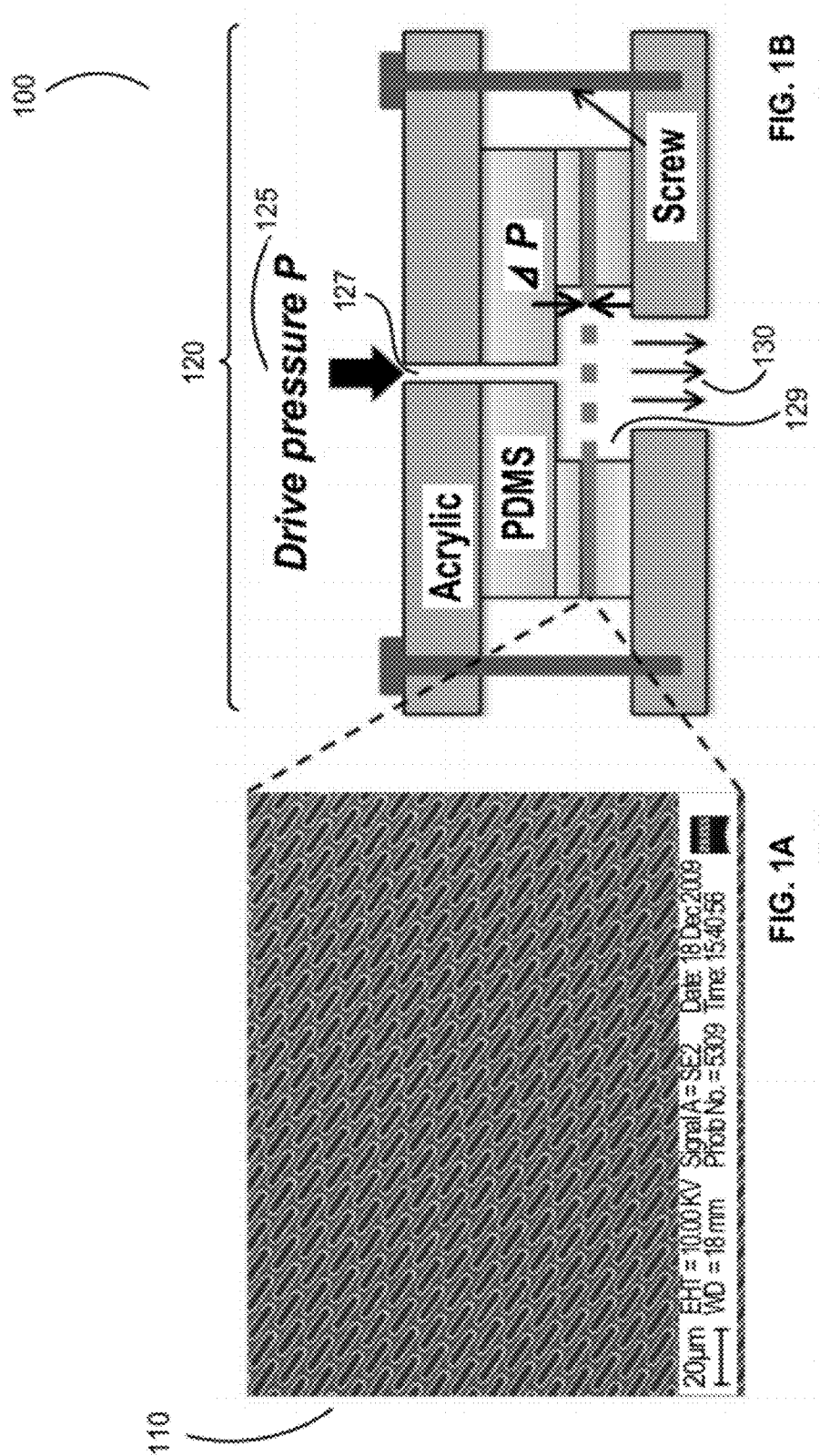

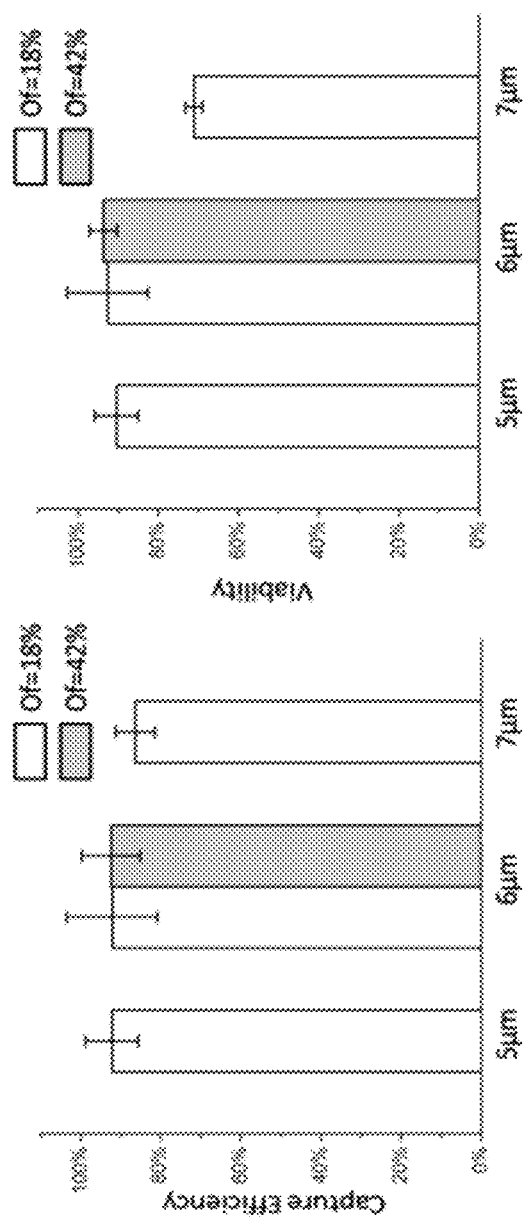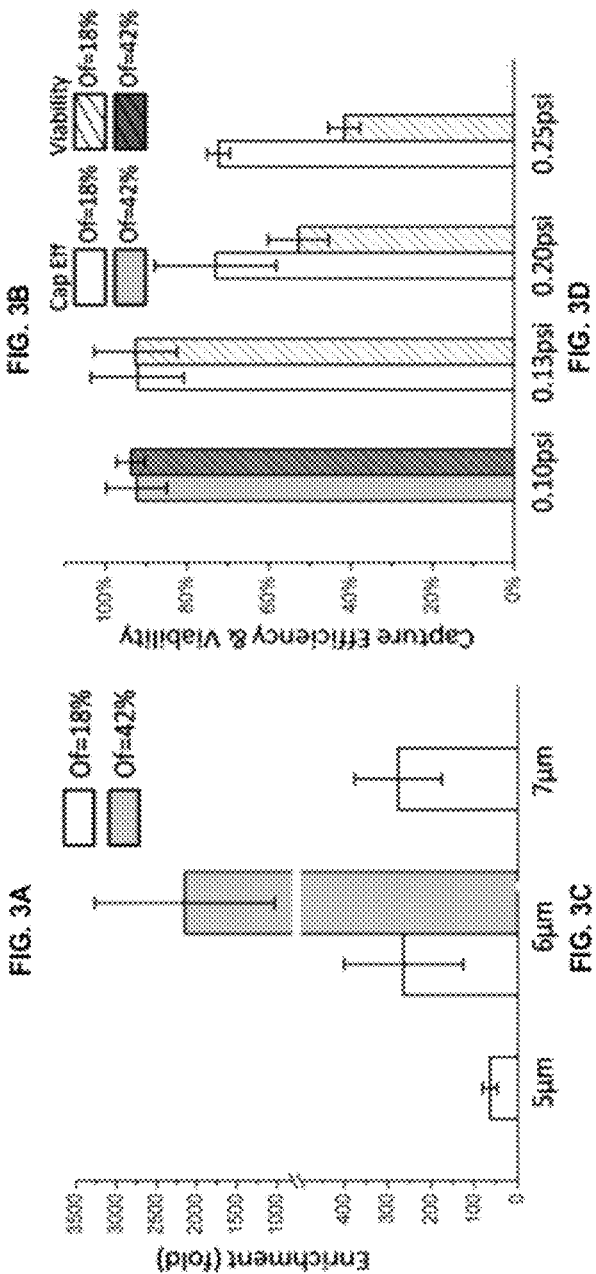

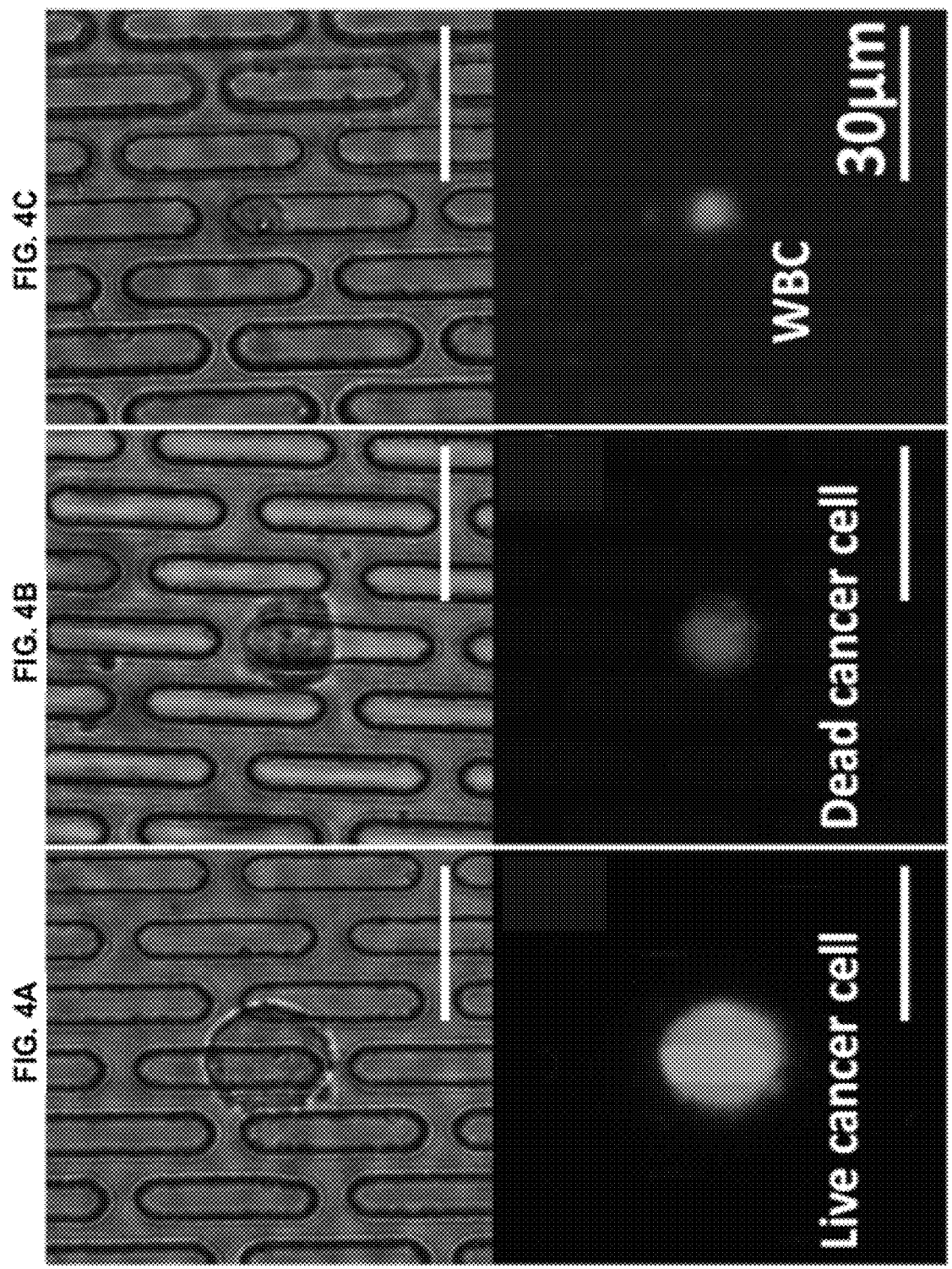

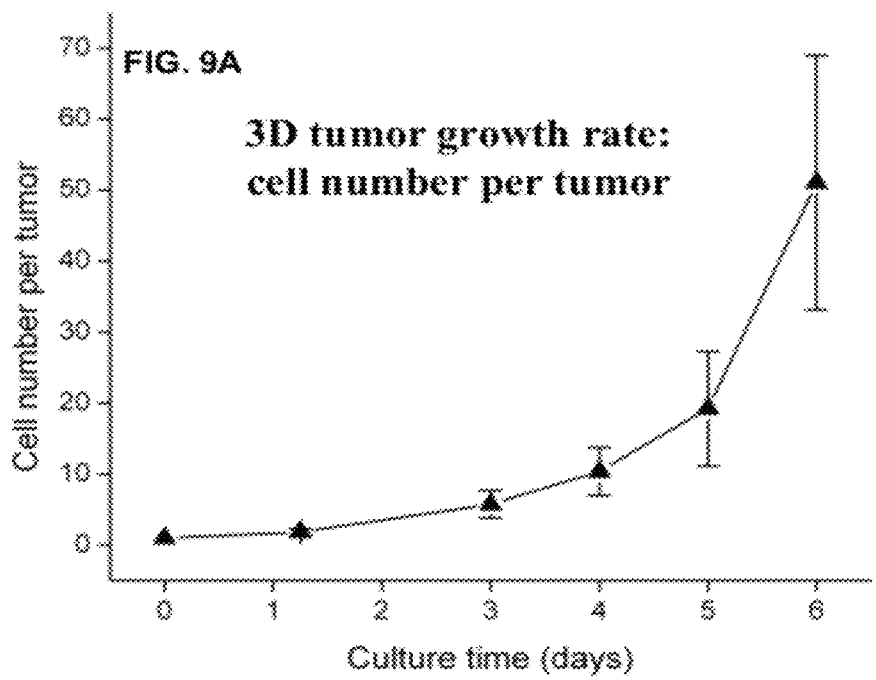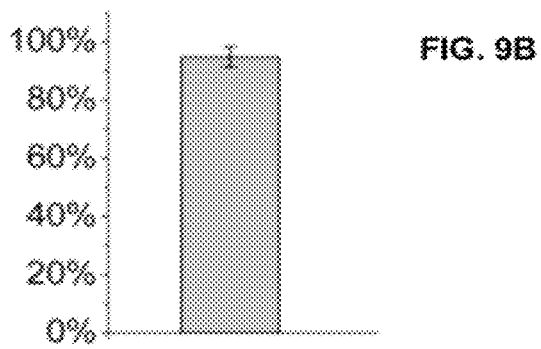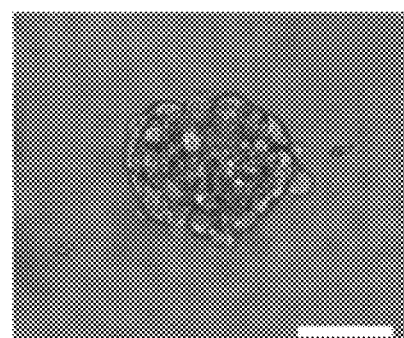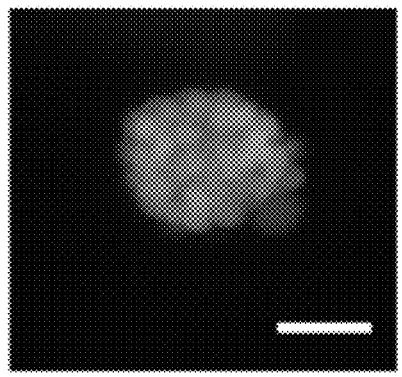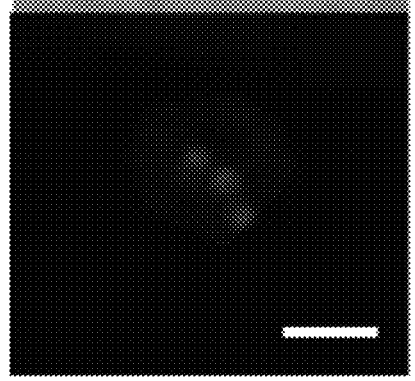

FIG. 11A
FIG. 11B
FIG. 11C
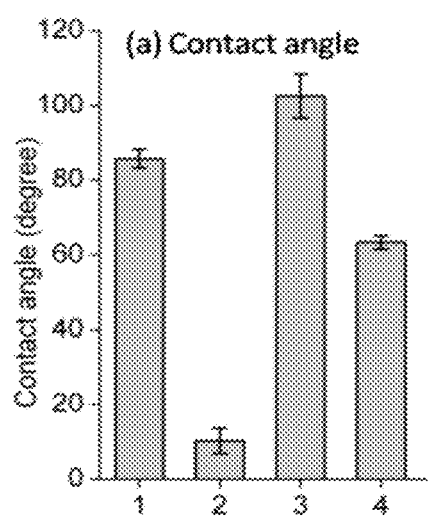
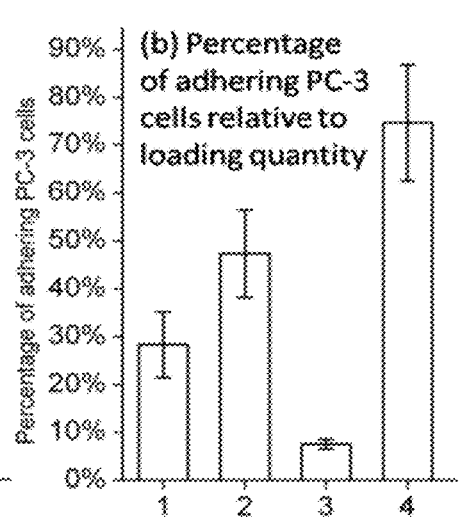
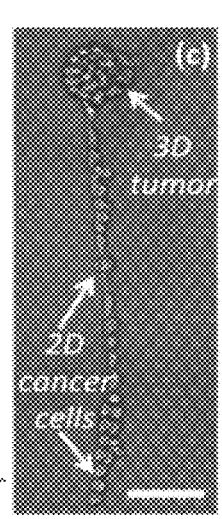

METHODS AND DESIGN OF MEMBRANE FILTERS

CROSS-REFERENCES TO RELATED APPLICATIONS

This application is a continuation-in-part of U.S. patent application Ser. No. 13/078,870, filed Apr. 1, 2011, and claims priority under 35 USC §119(e) to U.S. Provisional Patent Application No. 61/349,554, filed May 28, 2010, which are both herein incorporated by reference in their entireties for all purposes.

BACKGROUND OF THE INVENTION

Cancer metastasis is a leading cause of death for patients having solid-tumor cancers. Circulating tumor cells (CTCs) are tumor cells disseminated from the primary tumor into the bloodstream during metastasis. The presence of CTCs in peripheral blood has important clinical significance for early cancer diagnostics and patient treatment monitoring. Study of CTCs will also provide a valuable insight into the mechanism of tumor metastasis.

Most current CTC assays are either used for the enumeration of CTCs by immunostaining (Paterlini-Brechot, et al. *Cancer Lett.*, 2007, 253, 180-204; Zheng, et al. *J. Chromatogr., A*, 2007, 1162, 154-161; Nagrath, et al. *Nature*, 2007, 450, 1235-1239; Helzer, et al. *Cancer Res.*, 2009, 69, 7860-7866; Talasaz, et al. *Proc. Natl. Acad. Sci. USA*, 2009, 106, 3970-3975; Gleghorn, et al. *Lab Chip*, 2010, 10, 27-29), or for specific molecular analysis by quantitative PCR (qPCR) (Fizazi, et al. *Ann Oncol*, 2007, 18, 518-521; Xu, et al. *Cancer Res.*, submitted). For both applications, the main challenge is the extremely low concentration of CTCs (e.g. ~1/mL) in the patient peripheral blood. Therefore, an enrichment step of rare CTCs from a large volume (e.g. in the milliliter range) of patient blood sample is crucial for successful CTC study. Size based filtration has been explored for solid-tumor cancers because epithelial CTCs (15-30 µm in diameter) are generally much larger and less deformable than normal blood cells (Paterlini-Brechot, et al. *Cancer Lett.*, 2007, 253, 180-204; Zheng, et al. *Chromatogr., A*, 2007, 1162, 154-161; Xu, et al. *Cancer Res.*, submitted; Vona, et al. *Am. J. Pathol.*, 2000, 156, 57-63; Kahn, et al. *Breast Cancer Res. and Treat*, 2004, 86, 237-247; Zabaglo, et al. *Cytometry A*, 2003, 55, 102-108; Chen, et al. *Surf. Interface Anal.*, 2006, 38, 996-1003; Tan, et al. *Biomed Microdevices*, 2009, 11, 883-892; Kuo, et al. *Lab Chip*, 2010, 10, 837-842; Mohamed, et al. *J. Chromatogr., A*, 2009, 1216, 8289-8295).

Among various filter designs, membrane filters have the advantage of large efficient filtration area, which usually means short operation time (i.e. high throughput) (Paterlini-Brechot, et al. *Cancer Lett.*, 2007, 253, 180-204; Zheng, et al. *J Chromatogr., A*, 2007, 1162, 154-161; Xu, et al. *Cancer Res.*, submitted; Vona, et al. *Am. J Pathol.*, 2000, 156, 57-63; Kahn, et al. *Breast Cancer Res. and Treat*, 2004, 86, 237-247; Zabaglo, et al. *Cytometry A*, 2003, 55, 102-108). Both commercial track-etched polycarbonate membrane filters and micromachined parylene membrane filter with circular pores were previously reported and have been used in clinical trials for CTC detection. However, one major problem of the single-layer membrane filters is that fragile CTCs are easily damaged or even lysed during the filtration process, resulting in detection failure. For this reason, these works mainly focused on pre-fixed cells (Paterlini-Brechot, et al. *Cancer Lett.*, 2007, 253, 180-204; Zheng, et al. *J. Chromatogr., A*, 2007, 1162, 154-161; Vona, et al. *Am. J. Pathol.*, 2000, 156, 57-63; Kahn, et al. *Breast Cancer Res. and Treat*, 2004, 86, 237-247; Zabaglo, et al. *Cytometry A*, 2003, 55, 102-108), which disallowed further biological analysis requiring viable cells, such as genetic and chemotherapy studies, as well as cell culture applications. To address this problem, dual-layer 3D parylene membrane filters were reported for live capture of CTCs (Zheng, et al. *Proc. of Hilton Head* 2008, Hilton Head Island, S.C., USA, 2008, 134-137; Lu, et al. *Proc. of µTAS* 2009, Jeju, Korea, 2009, 588-590). Although they were able to maintain high viability of captured CTCs, the enrichment was too low because too many blood cells were trapped inside the filter gap.

Understanding the underlying biomechanics of viable CTC capture by filtration is of fundamental importance. However, by far most reports on CTC capture only focus on the design, testing and clinical trials of various kinds of special filtration devices. Only a few studies have been devoted to the fundamental work (Kuo, et al. *Lab Chip*, 2010, 10, 837-842.). Kuo et al. used an analytical method to study the biophysics of filtration, with emphasis on the pressure experienced by cells under various hydrodynamic environments during lateral-flow filtration (Kuo et al.). However, some important topics, such as the optimal filter geometry size, the safe range of transfilter pressure or inflow rate, and the quantitative measurements of enrichment and viability, are not provided.

Therefore, there remains a need to develop methods and systems that are capable of simple, yet highly efficient capturing of live tumor cells with high viability to overcome the above shortcomings. The present invention satisfies these and other needs.

BRIEF SUMMARY OF THE INVENTION

The present invention provides methods for designing a filtration system for capturing viable cells. In particular, the invention provides methods for maximizing the key parameters including pressure, filtration duration time, filter opening factor, hole size, shape and dimension and filtration to achieve capturing live cells with high efficiency and viability. In certain aspects, live cell capture has been realized by systematic tuning the key parameters of membrane filters. Prior to the advent of the present invention, it had not been possible to capture live cells on a membrane filter with high filtration efficiency and high cell viability. In one embodiment, the present invention provides a filter comprising a parylene membrane substrate. In another embodiment, the filter consists of a parylene membrane substrate.

A method for designing a filtration system for capturing viable cells at a high efficiency and high viability, the method comprising:
  providing a membrane filter consisting of a membrane substrate having a plurality of holes having a predetermined geometric design, the geometric design includes predetermined hole shape, dimension and filter opening factor;
  providing a pressure source coupled to the filter for applying pressure to a sample;
  maintaining a substantially constant transfilter pressure drop;

balancing (or choosing with a tradeoff between) the hole shape, filter opening factor, transfilter pressure and total filtration time in accordance with equations (I) and (II):

$$V(t) = \frac{\tau}{t}\left(1 - \exp\left(-\frac{t}{\tau}\right)\right) \quad (I)$$

wherein the viability of captured cells depends on the total filtration time t, and mean failure time τ, which is the time constant of lysis upon capture;

$$\text{Log}\tau = A + \frac{E^*(\sigma)}{k_B T} = A + \frac{\pi \gamma^2}{k_B T} \frac{1}{(\sigma + C)} \quad (II)$$

wherein:
V(t) is accumulative viability stands for the accumulative viability of captured cells;
t is total filtration time;
τ is the time constant of lysis upon capture;
E* is the free energy of the formation of a single hole;
σ is tension;
$k_B$ is the Boltzmann constant;
T is the absolute temperature;
γ is a line tension;
C is an energy term; and
A is a constant, to thereby obtain filtered viable cells.

In another aspect, the invention provides a method for isolating a viable tumor cell. The method includes obtaining a sample containing a viable tumor cell; and passing the sample under pressure through a membrane filter consisting of a membrane substrate having a plurality of holes having a predetermined geometric design including predetermined hole shape, dimension and filter opening factor for a time duration sufficient to isolate the viable circulating tumor cell. In one embodiment, the tumor cell is a circulating tumor cell. In another embodiment, the membrane substrate consists of a parylene substrate.

In yet another aspect, the invention provides a method for expanding filter-captured viable cells in culture. The method includes isolating a viable tumor cell from a sample by passing the sample containing the tumor cell through a membrane microfilter device under pressure for a time duration, wherein the microfilter device includes a membrane filter consisting of a membrane substrate having an array of holes with a predetermined dimension, shape and size; and proliferating the viable cells in culture. In one embodiment, the tumor cell is a circulating tumor cell. In another embodiment, the membrane substrate consists of a parylene substrate.

In still another aspect, the present invention provides a 3-dimensional tumor formed in vitro by proliferating a viable tumor cell in culture, wherein the viable tumor cell is isolated by passing a sample containing the tumor cell through a membrane filter under pressure for a time duration sufficient to isolate the viable tumor cell, wherein the membrane substrate consisting of a membrane substrate has a plurality of holes having a predetermined geometric design. In one embodiment, the tumor cell is a circulating tumor cell. In another embodiment, the membrane substrate consists of a parylene substrate.

In another aspect, the invention provides a method for enrichment of cells such as viable tumor cells (e.g., CTCs). The method includes passing a sample containing a tumor cell under pressure through a membrane filter consisting of a membrane substrate having an array of holes with a predetermined shape and dimension for a time duration sufficient to capture the viable tumor cell on the membrane filter, wherein the enrichment of the viable tumor cells is greater than 200-fold. In one embodiment, the tumor cell is a circulating tumor cell. In another embodiment, the membrane substrate consists of a parylene substrate.

In another aspect, the present invention provides a method for screening the efficacy of an anticancer drug. The method includes isolating a viable tumor cell; contacting the drug with the viable tumor cell; and determining the proliferation activity of the tumor cell in culture, wherein the viable tumor cell is isolated by passing the sample under pressure through a membrane filter consisting of a membrane substrate having a plurality of holes having a predetermined geometric design for a time duration sufficient to isolate the viable tumor cell. In one embodiment, the tumor cell is a circulating tumor cell. In another embodiment, the membrane substrate consists of a parylene substrate.

These and other aspects, objects and embodiments will become more apparent when read with the figures and detailed description which follows.

BRIEF DESCRIPTION OF THE DRAWINGS

FIGS. 1A-B illustrate an embodiment of a fabricated parylene membrane slot filter and filter assembly. (A) SEM picture of a slot filter with open-factor of 42%. (B) Filter assembly during constant-pressure-driven filtration.

FIGS. 3A-D illustrate filter characterization. Slot filters with open-factor of 18% and 42% were used in experiments. (A) Capture efficiency with slot width. (B) Viability with slot width. (C) Enrichment with slot width. Determined by testing of 18% open-factor filter, 6 μm is the optimal slot width. Filter with 42% had about one-order larger improvement on enrichment. (D) Capture efficiency and viability with transfilter pressure. The minimum possible transfilter pressures to process the whole blood sample are 0.13 psi and 0.10 psi for filters with 18% and 42% open-factor, respectively.

FIGS. 4A-C shows examples of captured cancer cells and the remaining WBC. (A) Live cancer cell could retain Calcein-AM. (B) Dead cancer cell was stained with PI, and the pre-labeled Calcein-AM dye leaked out. (C) Remaining WBC was stained with AO. A slot filter with slot size 6×30 μm and 42% open-factor was used here, and the transfilter pressure was 0.1 psi. Due to the large open-factor, few WBCs were left on the filter surface. Most remaining WBCs were stuck inside the slots. (all scale bars: 30 μm).

FIGS. 9A-E illustrates 3D on-filter cultured tumor growth rate and viability. (A) growth rate; (B) viability on the $6^{th}$ day; (C)-(E) bright field and fluorescence images of calcein-AM & PI stained tumor. (all scale bars: 40 μm).

FIGS. 11A-C illustrates Parylene surface treatment. 1: untreated parylene-C surface; 2: $O_2$ plasma treated parylene-C; 3: parylene-C with parylene-HT coating; 4: tissue culture polystyrene substrate. 11(A) shows contact angle measurement; 11(B) is an evaluation of cancer cell adhesiveness; 11(C) is without parylene-HT coating, some cancer cells adhered and proliferated on untreated parylene-C filter surface during 3D tumor culture with Matrigel. (scale bar: 100 μm).

DETAILED DESCRIPTION OF THE INVENTION

I. EMBODIMENTS

Figure 2A:
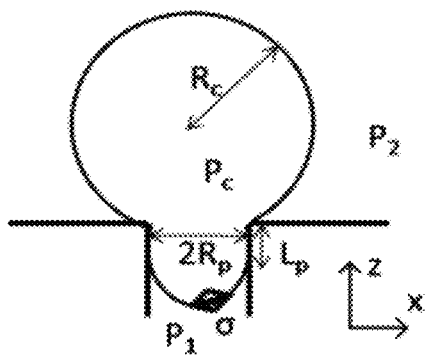
FIGS. 2A-D illustrate analytical and finite-element models of captured CTC. (A) and (B) are analytical cortical-liquid core models of CTC captured on pore and slot respectively. (C) and (D) are 3D FEM model of pore and slot filtrations respectively, built by COMSOL Multiphysics. The pore and slot filters used in (C) and (D) have the same open-factor. A transfilter pressure of 0.1 psi is applied as a boundary condition. The simulation results show the pressure distribution around the captured cells. Cell captured by slot is subject to a smaller trans-filter pressure drop.

The present invention provides methods for designing a filtration system for capturing viable tumor cells such as CTCs, at a high efficiency and high viability, methods for isolating viable tumor cells, methods for enrichment of viable tumor cells; methods for screening the efficacy of an anticancer drug, and methods for expanding filter-captured viable cells in culture. The methods involve passing a sample under pressure through a membrane filter consisting of a membrane substrate having a plurality of holes having a predetermined geometric design for a time duration sufficient to isolate the viable tumor cells. The predetermined geometric design includes predetermined hole shape, dimension and filter opening factor.

In certain aspects, the present invention is based upon a study of the biomechanics of viable tumor cells, such as circulating tumor cells (CTCs), captured using membrane filters. It is supported with extensive experimental results using low-pressure filtration through the specially designed slot filters made of parylene-C. In addition, in certain aspects, the present invention provides an in-depth modeling and theoretical analysis of viable CTCs captured from blood on a membrane filter. With both experiments and theories, a set of "key engineering design parameters" that achieve high CTC viability have been developed. These design parameters include for example, the filter geometry design, fluid delivery method, transfilter pressure and total filtration time. The time-dependent rupture of cell membranes and the loss of viability during filtration are presented by both molecular model and the Griffith's failure theory. In certain aspects, the present invention provides a "golden zone" for high CTC viability filtration, with respect to filtration transfilter pressure and time.

In certain instances, other types of cells are suitable for use in the present invention. A skilled person will appreciate that other kinds of cells include, but are not limited to, fetal cells, white blood cells, red blood cells, other epithelial cells and the like, where size-based enrichment or isolation from solution or cell mixtures (e.g., blood, body fluid or PBS) is possible. The methods allow for cells to be captured as viable cells using for example tension, stress and time, and this applies to all live cells, even plant cells.

The present invention provides a profound understanding of the mechanism of CTC capture by single-layer parylene membrane filters and exploiting the "key parameters" required for high viability. Filtrations through pore and slot filters were modeled and compared by analytical methods. Surprisingly, it was found that in certain instances, filter hole opening size, transfilter pressure, open-factor and fluid delivery methods all have influences on the viability of captured CTCs. When processing samples of large volume, a time-dependent viability drop during filtration is observed, which is reasonably explained by both a viscoelastic model and a molecular model. More importantly, for the first time, a "golden zone," is disclosed with respect to filtration transfilter pressure and time, allowing for viable CTC capture, which can be used as guidance in membrane filter design and operation. As one demonstration and application of the high viability of captured CTCs, successful further cell culture after filtration is achieved. Captured cancer cells showed significant proliferation in both 2D and 3D cultures.

In general, a 2D culture represents cells that are cultured in a monolayer, which is the traditional or typical cell culture method. However, a skilled artisan will appreciate that unlike an in vivo tumor, a 2D culture cannot represent certain features of a real tumor due to its morphology differences. In contrast, a 3D culture means cells that grow into a 3D scaffold using for example, matrigel or collagen to form a 3D spherical tumor. In general, a 3D tumor is a better surrogate for a natural or in vivo tumor.

As used herein, the term "parylene" includes a polymer having formulae I, II, and III or combinations thereof. The polymer can be a homopolymer, a copolymer, a polymer blend or combinations thereof. $R^1$, $R^2$, $R^7$ and $R^8$ are each independently H, alkyl, heteroalkyl, aryl or halogen. The alkyl can be a $C_1$-$C_6$ hydrocarbon radical. The halogen is Cl, F, Br, or I. Heteroalkyl is an alkyl substituent containing at least one heteroatom, such as O, S, N, Si or P.

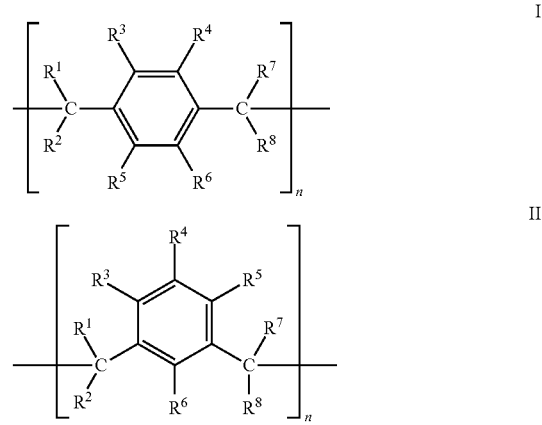

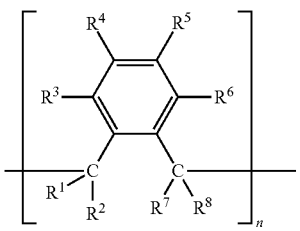

III $R^3$-$R^6$ are each independently H, alkyl, aryl, halogen, heteroalkyl, hydroxyl, amino, alkylamino, arylamino, aroylamino, carbamoylamino, aryloxy, acyl, thio, alkylthio, cyano, alkoxy. An alkyl group can be a substituted alkyl having up to 29 carbon atoms. A substituted alkyl can be mono- or polyunsaturated alkenyl or alkynyl radical having in each case up to 29 carbon atoms, i.e., a substituted $C_1$-$C_{29}$alkyl, $C_2$-$C_{29}$alkenyl or $C_2$-$C_{29}$alkynyl radical. Suitable substituents are also cyclic radicals. The substituted alkyls can be methyl, ethyl, or propyl radical, carrying one or more identical or different radicals. Depending on the nature of the substituents, these can be attached via a single or multiple bond or in a spiro form. Preferred subtituents are halogen, such as Cl, F, Br or I, amino, lower alkylamino, lower alkanoylamino, aroylamino, such as, in particular, benzoyl amino, hyroxyamino, hydroxyimino, lower alkoxyamino, aroxyamino, such as, in particular, phenoxyamino. Lower alkylthio includes $C_1$-$C_6$alkylthiols. Aryloxycarbonyl includes phenoxycarbonyl, benzyloxycarbonyl, hydroxyaminocarbonyl, aminoacylamino, carbamoyl, amidino. Aryoxy can be phenyloxy, aminocarbonyl-oxy, oxo, aminosulfonyl and lower alkylsulfonyl-amino. Heteroalkyl is an alkyl substituent having one or more heteroatoms in the alkyl substitutents, in particular, mercaptoalkyl having up to 29 carbon atoms, aminoalkyl, phosphinoalkyl, haloalkyl, hydoxyalkyl or silylalkyl. Preferably, parylene has a structure represented by the formula I. In addition, preferred parylene also includes commercially available parylene, C, F, A, AM, N, and D.

In certain other aspects, parylene-C and parylene-HT are preferred parylene derivatives, whose structures are shown below:

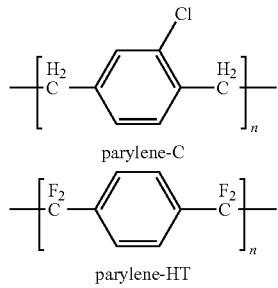

parylene-C parylene-HT

As used herein, the term "monodispersed" refers to the openings or holes on the membrane filter having substantially identical size, dimension and shape.

As used herein, the term "figure of merit" provides a measure of the efficiency of the filtration device. A large figure of merit number is an indication of higher filtration efficiency. Figure of merit is defined as the recovery rate divided by time. Recovery rate is defined as particles recovered divided by the total number of target particles. The time used in the calculation of figure of merit is the total processing time to conduct the testing. For example, in one embodiment, the parylene filter of the present invention has a figure of merit of greater than or equal to 890 and/or having a Young's modulus≈4 GPa.

The term "sample" as used herein includes any biological specimen obtained from a patient, a subject, a mammal or plant. Samples include, without limitation, circulating tumor cells, whole blood, plasma, serum, red blood cells, white blood cells (e.g., peripheral blood mononuclear cells), saliva, urine, stool (i.e., feces), sputum, bronchial lavage fluid, tears, nipple aspirate, lymph (e.g., disseminated tumor cells of the lymph node), fine needle aspirate, any other bodily fluid, a tissue sample (e.g., tumor tissue) such as a biopsy of a tumor (e.g., needle biopsy), and cellular extracts thereof. In some embodiments, the sample is whole blood or a fractional component thereof such as plasma, serum, or a cell pellet. In preferred embodiments, the sample is obtained by isolating circulating cells of a solid tumor from whole blood or a cellular fraction thereof using any technique known in the art. In other embodiments, the sample is a formalin fixed paraffin embedded (FFPE) tumor tissue sample, e.g., from a solid tumor of the lung, colon, or rectum.

As used herein, the term "circulating tumor cells" ("CTCs") comprises extratumoral cells that have either metastasized or micrometastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.).

As used herein, the term "cell viability" is a determination of living cells and/or dead cells, based on a total cell population. Cell viability measurements are used herein to evaluate the death or life of cancerous cells (in the presence or absence of treatment) and for example, the rejection of implanted organs. In other applications cell viability tests, the filter herein can be used to evaluate environmental damage due to toxins.

Parylene is a USP Class VI biocompatible polymer that can be deposited through a highly-conformal vapor deposition process. Types of parylene include parylene C, F, A, AM, N, and D. Of the three most common types of parylene shown below, parylene C is perhaps the most widely used in industry. The advantages of the use of parylene include its proven biocompatibility, its strength, elasticity and flexibility (e.g., Young's modulus≈4 GPa), its conformal pinhole-free room-temperature deposition, its low dielectric constant (≈3) high volume resistivity (>$10^{16}$ Ω-cm), its transparency, and its ease of manipulation using standard microfabrication techniques such as reactive ion etching (RIE). In certain embodiments, the parylenes used in the present invention have Young's modulus of at least 4 GPa. Several research groups have used parylene C deposition as a method of creating a biocompatible, water-blocking seal around electrode arrays typically fabricated using a polyimide substrate. This is necessary because most polyimides have a moisture absorption that is more than an order of magnitude higher than that of parylene C. Some specialized polyimide films have lower moisture absorption, but they require high-temperature curing steps.

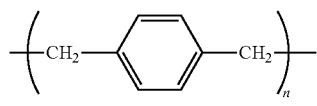

Parylene N

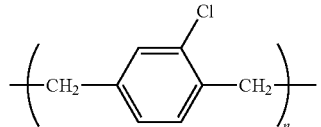

Parylene C

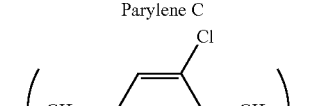

Parylene D

Parylene microfilters have found various applications. Parylene microfilter devices with predetermined geometric design have been described in U.S. Pat. No. 7,846,393, incorporated herein by reference. Use of parylene microfilters for various biological applications has been described in U.S. Pat. No. 7,846,743 and PCT Patent Publication No. WO2006/116327, each of which is incorporated herein by reference. Parylene microfilters with a top and a bottom porous membranes for separating circulating tumor cells have been described in U.S. Patent Publication No. 2009/0188864, which is incorporated herein by reference.

Although parylene is a preferred choice of materials for the membranes, the filter material is not limited to parylene. Other suitable materials include, for example, polymer filter materials, such as nylon, polyester, polystyrene, polypropylene, polycarbonate, Teflon, PDMS, and the like. In addition, other non-polymer filter materials, such as silicon, silicon dioxide, metals, such as inert metals are also suitable.

In some embodiments, the isolated cells have a viability of greater than 50%, 55%, 60%, 65%, 70%, 75%, 80%, 85%, 90%, 91%, 92%, 93%, 94%, 95%, 96%, 97%, 98% or even 99%. In one embodiment, the viability of the isolated cells is greater than 95%.

A skilled person will appreciate that in certain instances, viability is dependent on pressure and filtration. Thus, if the pressure is low and the time is short, it is possible to achieve essentially 100% viability of the cells.

In one aspect, the present invention provides a method for designing a filtration system for capturing viable cells at a high efficiency and high viability, the method comprising:
providing a membrane filter consisting of a membrane substrate having a plurality of holes having a predetermined geometric design, the geometric design includes predetermined hole shape, dimension and filter opening factor;
providing a pressure source coupled to the filter for applying pressure to a sample;
maintaining a substantially constant transfilter pressure drop;
balancing (or choosing with a tradeoff between) the hole shape, filter opening factor, transfilter pressure and total filtration time in accordance with equations (I) and (II):

$$V(t) = \frac{\tau}{t}\left(1 - \exp\left(-\frac{t}{\tau}\right)\right) \quad (I)$$

$$\text{Log}\tau = A + \frac{E^*(\sigma)}{k_B T} = A + \frac{\pi \gamma^2}{k_B T} \frac{1}{(\sigma + C)} \quad (II)$$

wherein:
V(t) is accumulative viability of captured cells;
t is total filtration time;
τ is the time constant of lysis upon capture (so the longer the cells stay on the filter under the transfilter pressure, the lower is the cell viability);
E* is the free energy of the formation of a single hole;
σ is tension;
$k_B$ is the Boltzmann constant;
T is the absolute temperature;
γ is the line tension (along the perimeter of a pore on the cell membrane; the pore is created by the membrane tension, σ);
C is an energy term; and
A is a constant, to thereby obtain filtered viable cells.

In one aspect, the present invention provides for the following numerical values:

For V(t), which is accumulative viability, the value is between 0.1% to about 99.0% such as 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%.

Figure 5:
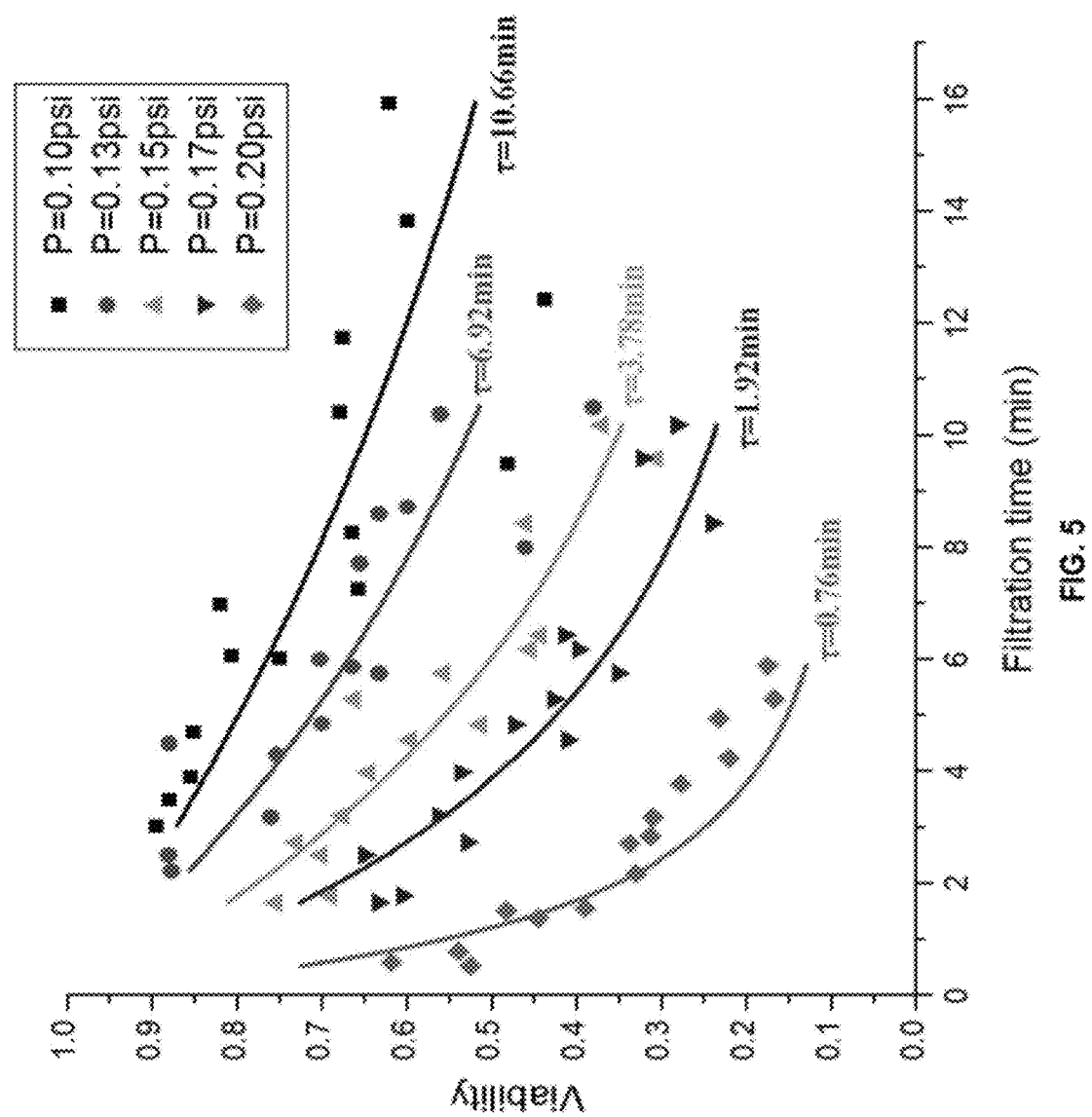
FIG. 5 shows a time-dependent viability drop. The time constants of lysis were obtained by fitting the experimental data into Eq. 17; and shows a relationship between total filtration time and sample volume.

For t, the value is about 1 sec to about 20 min such as 1 sec, 5 sec, 10 sec, 15 sec, 20 sec, 25 sec, 30 sec, 40 sec, 45 sec, 50 sec, 55 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 30 min, or 60 min. In certain instances, the value of t can be 21 minutes to 2 hours, such as 25 min, 30 min, 35 min, 40 min, 45 min, 50 min, 55 min, 60 min (1 hour), 1.5 hours or even 2 hours. Typically, the value for t is dependant on sample volume. As is shown in FIG. 5B, a 1 mL sample needs about 0.5 to about 4 min, whereas a 5 mL sample needs about 4.5 to about 16 min. The total filtration time depends on both transfilter pressure and sample volume and can be adjusted to yield superior viability. In certain aspects, larger or smaller volumes can be proportional to the values in FIG. 5B. A skilled artisan will appreciate that according to Equation I and II, one preferred choice is a large filter opening factor, large filter area, low transfilter pressure (which translates to small σ and large τ), and small filtration time.

Figure 6A:
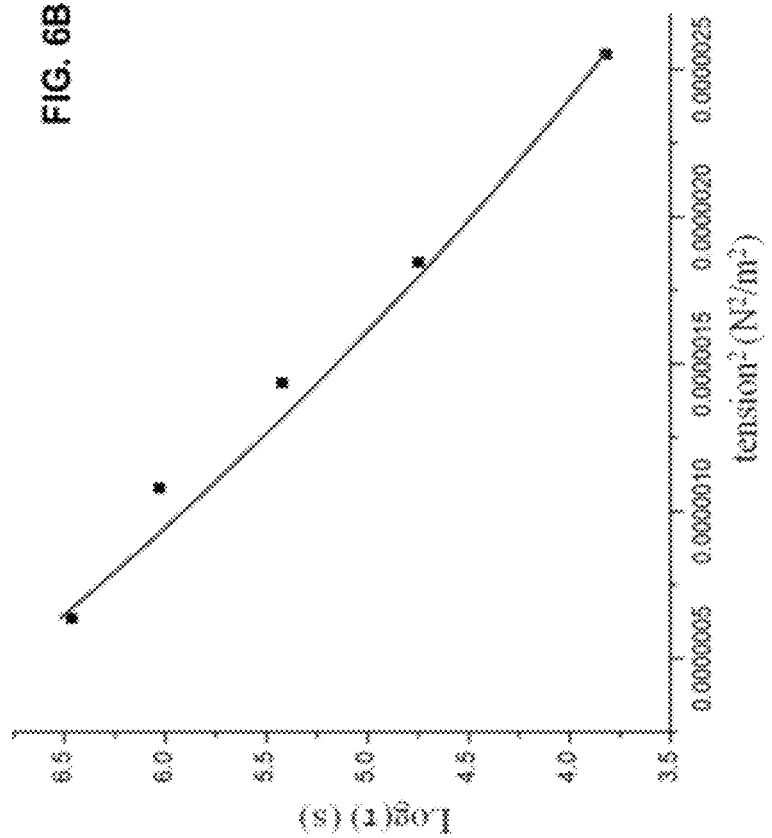
FIGS. 6A-B show relationships between Log(τ) and tension according to (A) the molecular model, and (B) the Griffith's failure model, respectively. Experimental data are fitted into Eq. 20 and Eq. 28, respectively.
Figure 6B:
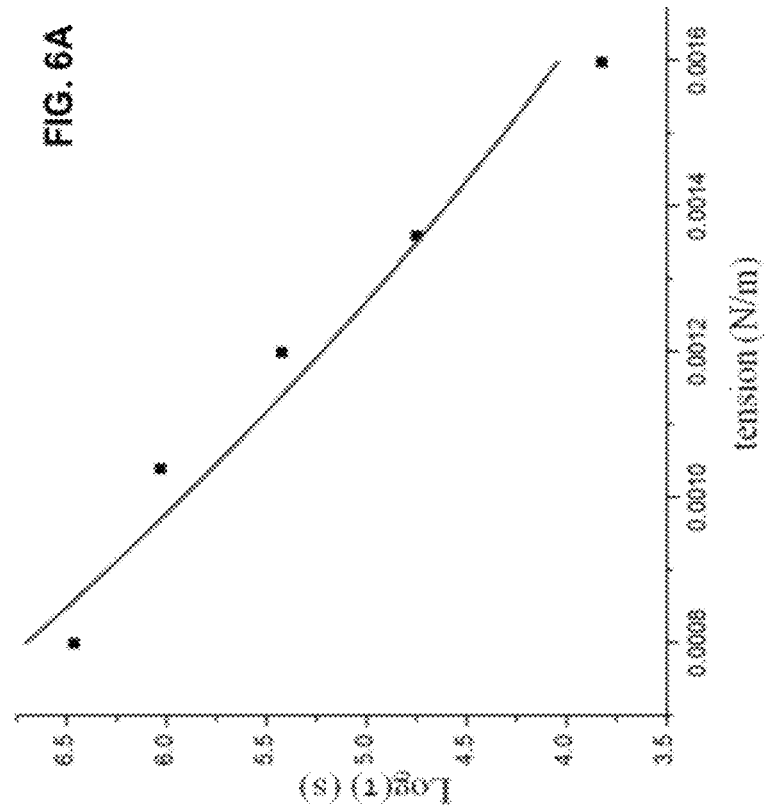

For τ, the value is about 1 sec to about 20 min such as 1 sec, 5 sec, 10 sec, 15 sec, 20 sec, 25 sec, 30 sec, 40 sec, 45 sec, 50 sec, 55 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, or 20 min. As is shown in FIG. 6A-B, a larger tau is related to a smaller transfilter pressure. For example, when the transfilter pressures are 0.10, 0.13, 0.15, 0.17, 0.20 psi, the value for r is 10.66 min, 6.92 min, 3.78 min, 1.92 min and 0.76 min, respectively. A skilled artisan will appreciate that according to Equation I and II, one design is a system with a τ value larger than 20 min (for a small transfilter pressure, and hence a small σ) can be accomplished by using a larger filter area.

For E*, the values is the free energy of the formation of a single hole. For example, $E=0.04329 \ k_B T$ for the molecular membrane model and $E=0.02485 \ k_B T$ for the Griffith's model. $k_B$ is the Boltzmann constant and T is absolute temperature.

For σ, the values can be taken from FIG. 6A and 6B, for the molecular membrane model and Griffith's model respectively. A skilled person will understand that these experimental results can be prepared for other systems as well. In FIG. 6A, the values for tension ranges from about 0.0008 to about 0.0016 N/m for the molecular membrane model and as shown in FIG. 6B, the value ranges from about 0.0000005 to about 0.0000025 $N^2/m^2$ for the Griffith's model. Those skilled in the art will appreciate other values for σ include about 0.0008 N/m to about 1.0 N/m such as about 0.00016 to about 1.0 N/m for the molecular membrane model and about 0.0000005 $N^2/m^2$ to about 1.0 $N^2/m^2$ such as about 0.0000025 $N^2/m^2$ to about 1.0 $N^2/m^2$ for the Griffith's model.

For $k_B$, the value is equal to $1.3806504 \times 10^{-23}$ $JK^{-1}$.

For T, the value is between 273°K to about 310°K such as 275°K, 280°K, 285°K, 290°K, 295°K, 300°K, 305°K, or 310°K.

For γ, the value is between $1 \times 10^{-8}$ to about $1 \times 10^{-12}$ such as $1 \times 10^{-8}$, $1 \times 10^{-9}$, $2 \times 10^{-9}$, $3 \times 10^{-9}$, $4 \times 10^{-9}$, $5 \times 10^{-9}$, $6 \times 10^{-9}$, $7 \times 10^{-9}$, $8 \times 10^{-9}$, $9 \times 10^{-9}$, $1 \times 10^{-10}$, $2 \times 10^{-10}$, $3 \times 10^{-10}$, $4 \times 10^{-10}$, $5 \times 10^{-10}$, $6 \times 10^{-10}$, $7 \times 10^{-10}$, $8 \times 10^{-1}$, $9 \times 10^{-10}$, $1 \times 10^{-11}$, $2 \times 10^{-11}$, $3 \times 10^{-11}$ $4 \times 10^{-11}$, $5 \times 10^{-11}$, $6 \times 10^{-11}$, $7 \times 10^{-11}$, $8 \times 10^{-11}$, $9 \times 10^{-11}$, or $1 \times 10^{-12}$.

For C, the value is 0.00243 N/m.

For A, the value is −6.70 for the molecular membrane model or −6.72 in the Griffith's model.

In certain aspects, the term "balance" as used herein includes the concept that to achieve a desirable viability, the various parameters place restrictions on each other such as tradeoffs. For example, to keep a certain cell viability, increased transfilter pressure will allow for a shorter total filtration time. For a longer total filtration time, a lower transfilter pressure is desirable. In certain other aspects, with a longer total filtration time and low pressure an increased "filter opening factor" is desirable to maintain cell viability. In addition, the total filtration time can be reduced if the filter opening factor is high. In other aspects, the viability of captured cells depends on the total filtration time t and mean failure time τ. A balance of various parameters of the equations will allow for the desired cell viability by choosing a tradeoff between hole shape, filter opening factor, transfilter pressure and total filtration time in accordance with Equations (I) and (II).

A skilled artisan will appreciate that Equations I and II are useful to teach how to control the final accumulative viability of cells captured on the filter after a certain amount of liquid volume (containing targeted cells) is filtered through a filter. First, Equation II teaches that the physics of cell damage (toward lysis) originates from membrane tension, σ. Therefore, once a cell is captured, membrane tension, σ, is induced by the transfilter pressure. This membrane tension, σ, will then induce many pores (in nanometer size). If the tension continuously exists, certain pores can expand (by thermal energy) beyond a critical size and lead to the irreversible membrane breakdown and cell death. As a result, the time constant of the cell lifetime, τ, can be calculated from Equation II, which teaches that the larger the membrane tension, the shorter the lifetime of the cells after capture.

With Equation II, Equation I can then be derived with the information of volume of liquid containing targeted cells and the total filtration time. Basically, Equation II teaches that the larger the cell membrane tension, the smaller the cell lifetime upon capture and transfilter pressure. Here, the larger the transfilter pressure gives larger cell membrane tension. Equation I teaches that, in order to get high cell viability, choose a large τ (or low transfilter pressure) and small total filtration time. This also translates to large filter opening factor and filter area.

In certain aspects, the present invention provides a large filter opening factor, large filter area, low transfilter pressure (which translates to small σ and large τ), and small total filtration time. These factors together translate to the final accumulative viability of the captured cells, which is governed by Equation I and II.

In certain aspects, the viability of captured cells depends on the total filtration time t, and also a term of mean failure time τ (the time constant of lysis upon capture). τ is related to the membrane tension, and energy of forming a pore follows the Boltzmann distribution. In certain aspects, the mean failure time T is related to the membrane tension.

In one embodiment, the tumor cell is a circulating tumor cell. In another embodiment, the membrane substrate consists of a parylene substrate. In one embodiment, an isolated cell has a viability of greater than 90%. In another embodiment, the plurality of holes has a rectangular shape. In yet another embodiment, the plurality of holes has a dimension of 6 μm by 40 μm. In one embodiment, the pressure is between 0.01 psi and 0.2 psi. In some embodiments, the sample is passed through the parylene membrane filter in about 1 second to about 600 seconds. In certain other embodiments, the total filtration time is 1 second to 30 minutes depending on the transfilter pressure and sample volume. Of course, the membrane filter does not need to be parylene. In other embodiments, the sample is passed through the parylene membrane filter between 100 seconds to 600 seconds/1 mL of blood optionally spiked with cancer cells, such as 100, 150, 200, 250, 300, 350, 400, 450, 500, 550 or 600 seconds/1 mL. In other embodiments, the membrane filter has an opening-factor between 10% and 50%, such as 10, 15, 20, 25, 30, 35, 40, 45, 50%, 60%, 70%, 80%, 90, or even 99.9%. In other instances, the opening-factor can be any value from 0.1-99%.

The membrane filter, such as a parylene membrane filter, comprises a plurality of holes of a predetermined geometric design formed in, and penetrating, the parylene membrane. The geometric design includes, for example, a size, a shape and density. In one embodiment, the design of the membrane is such that CTCs are selectively captured or retained by the membrane, while other cells and materials in the blood pass through the membrane selected according to their size and shape. The efficiency of the membrane filter can be adjusted by changing the size, shape, density of the holes on the membrane and the pressure applied to the sample to be filtered. In some preferred embodiments, the filter of the present invention has a figure of merit up to 890. In other embodiments, the parylene membrane filter has a figure of merit between about 800 to about 890. In some preferred embodiments, the holes are monodispersed.

The predetermined geometric design is according to any one or more of size, shape, density, uniformity, and arrangement of holes in the parylene membrane. In some embodiments, the holes themselves can have rounded or sharp corners. The holes can be of a regular shape (e.g., circles, ovals, ellipses, squares, rectangles, symmetrical and unsymmetrical polygons, rods) or any other shape desired, including, but not limiting to, other irregular shapes. The holes can be of different sizes and shapes. The holes can all be of uniform size and/or shape. In some preferred embodiments, the holes may be limited to a predetermined range of sizes and/or shapes. In some embodiments, membrane filter has a hole shape selected from the group consisting of a circular, an elliptical, a symmetrical polygonal, an unsymmetrical polygonal, an irregular shape and combinations thereof. In a preferred embodiment, the holes have a rectangular shape and arranged uniformly. In some embodiments, the holes can be arranged in a uniform grid or array (e.g., one or more rows and/or columns, concentric circles, and the like). Preferably, holes are all of the same shape and size and may also be of uniform density or pattern on the membrane, aside from the edges.

The predetermined geometric designs are not limited to known designs, as the methods are applicable to all geometries. In certain instances, the methods comprise membrane tension and total filtration time, so the shape of the efflux is not necessarily regular geometricx design. Circular or hexagonal holes, or any other shapes, are suitable as long as fluid-mechanical calculation is performed to derive the pressure differential across the filter, and hence translated tension stress to the cell membrane.

The holes can be of any desirable size and shape which will determine the ability of a particle or cell of interest to pass through. For instance, in some embodiments, the holes can have a minimum or maximum cross sectional length of 1, 2, 3, 4, 5, 8, 10, 12, 14, 16, 18, 20, 24, 28, 30, 32, 36, 40, 45, 50 microns or more. In some embodiments, the holes are circles, ovals, rectangles or polygons. In some further embodiments, the circular holes have diameters of 2, 4, 8, 10, 14, 20, 30, 40, 50 microns or more. In other further embodiments, the holes are oval and have different lengths and widths which may be independently be selected from 2, 4, 6, 8, 10, 14, 20, 30, 40 or 50 microns. For instance, in some further embodiments, the holes may be circles from 6 to 10, 5 to 12, 10 to 20, 8 to 40, or 6 to 60 microns in diameter. In some preferred embodiments, the holes are rectangles whose dimensions are from 2 to 10 microns by 30 to 60 microns, from 4 to 9 microns by 35 to 50 microns, from 5 to 8 microns by 35 to 45 microns, or from 5 to 7 microns by 35 to 45 microns. In a more preferred embodiment, the holes are from 6 by 40 microns. In some embodiments, the minimum width of the rectangular holes is 1, 2, 4, 5, 5.5, 6, 6.5, 7, 8, 9 or 10 microns and the minimal length of the rectangular holes is 30, 31, 32, 33, 34, 36, 38, 39, 40, 41, 42, 43, 44, 45, 46, 48, 50 microns. In some embodiments, the width of the rectangular holes is 1, 2, 4, 5, 5.5, 6, 6.5, 7, 8, 9 or 10 microns and the length of the rectangular holes is 30, 31, 32, 33, 34, 36, 38, 39, 40, 41, 42, 43, 44, 45, 46, 48, 50 microns. In some embodiments, of any of the above the maximum length of the hole is 50, 60, 70, 80, 90, 100 microns or 200 microns.

In one embodiment, for rectangular hole, a width of about 3 to about 10 microns, such as about 6 μm width works well. In certain aspects, the length is not critical, as long as the exit hole is larger than the cell diameter (otherwise the cells will fully "block" the hole).

The holes may also be defined according to their cross sectional area and/or shape. The shapes can be as any described above, preferably, the shapes are rectangle. In some embodiments, the cross sectional areas range from about 1 to 1000 square microns, 1 to 10 square microns, 10 to 100 square microns, 25 to 500 square microns, 50 to 400 square microns, 75 to 150 square microns, 75 to about 500 square microns or 200 to 1000 square microns. In certain embodiments, the cross sectional areas range from 50 to 300 square microns, 100 to 200 square microns, 200 to 240 square microns, 150 to 300 square microns, 200 to 280 square microns or 200 to 400 square microns. In one embodiment, the holes have a slot/rectangular shape and a cross sectional area of 240 square microns. In any of the above, the holes can be monodispersed. In any of the above, the parylene membrane filter can have a figure of merit up to 890, and preferably from 800 to 890.

In some embodiments, the membrane filter, such as a parylene membrane filter has a hole density of from 1 to 40,000, 1,000 to 40,000, 5,000 to 40,000, 6,000 to 40,000, 7000 to 40,000, 10,000 to 40,000; 10,000 to 30,000; 20,000 to 30,000; 20,000 to 40,000; or 30,000 to 40,000 holes per square millimeter. In certain instances, the parylene membrane filter has an array of rectangle holes with a hole density from 1 to 1000, 1 to 900, 1 to 850, 1 to 800, 1 to 700, 1 to 600, 100 to 1000, 300 to 1000, 500 to 900, 400 to 800, or 600 to 900 holes per square millimeter. In one instance, the parylene membrane filter has an array of rectangle holes with a hole density of 100, 200, 300, 400, 500, 600, 700, 800, 850, 900 or 1000 holes per square millimeter. In certain embodiments, the hole density is at least 1, 10, 100, 200, 300, 400, 500, 600, 700, 800, 900, 1000, 2000, 3000, 4000, 5000, 6000, 7000 or 8000 holes per square millimeter. In a preferred embodiment, the parylene membrane filter has 30401 or more holes per 36 square millimeters. Such hole densities depend in part upon the sizes of the holes, with smaller holes allowing for greater densities. The densities can be adjusted so as to insure that the holes do not fuse together during manufacture and the strength of the parylene membrane remains suitable. A thicker membrane can be used to strengthen the membrane at higher hole densities.

In certain embodiments, the number and size of the holes affects the rate at which a sample can pass through the membrane and the strength of the membrane. The density of the holes is typically range from 1,000 to 40,000 holes per square millimeter. The plurality of holes can provide an opening area ratio of from 4% to 60%, including ranges from 4% to 25%, 5% to 25%, 10% to 25%, 10% to 50%, 15% to 30%, 5% to 45%, 10% to 50%, 15% to 45%, 20% to 40%, 25% to 50%, and 45% to 60%. In some embodiments, the area opening ratio is at least 1%, 2%, 4%, 5%, 8%, 10%, 12%, 13%, 14%, 15%, 17%, 18%, 19% or 20%. In one embodiment, the area opening ratio is 18%.

In some embodiments of the above, the membrane filter, such as a parylene membrane filter is from 0.5 to 20 microns thick. In some preferred embodiments, the membrane is at least 1, 2, 3, 4, 5, 6, 7, 8, 9, 10, 11, 12, 13, 14, 15 or 16 micron thick. In other embodiments, the membrane filter is from 1 to 20 microns thick, in more preferred embodiments, the membrane filter is from 1 to 4, 5 to 10, 5 to 15, 8 to 15 or 10 to 20 microns thick. In one embodiment, the parylene membrane filter has a thickness of 10 microns. The thickness of the membrane filter is a compromise between membrane strength and flow resistance through the membrane. Accordingly, as increasing hole density reduces membrane strength, membranes having a greater number of holes typically require a thicker membrane than membranes having a fewer number of the same holes.

In some embodiments, a constant pressure can be applied to the sample to facilitate the filtration process, preferably, a constant low drive-pressure is applied to the sample. The transfilter pressure can range from about 0.0001 psi to about 3 psi, preferably about 0.01 to 2 psi or 0.01 to 0.5 psi, preferably from 0.05 to 0.4 psi, more preferably from 0.1 to 0.3 psi and even more preferably from 0.1 to 0.25 psi. In one embodiment, the constant pressure is 0.1, 0.11, 0.12, 0.13, 0.14, 0.15, 0.16, 0.17, 0.18, 0.19, 0.2, 0.21, 0.22, 0.23, 0.24 or 0.25 psi. In another embodiment, a constant pressure applied to the sample is 0.1, 0.11, 0.12, 0.13, 0.14, 0.15, 0.16, 0.17, 0.18, 0.19, 0.2, 0.21, 0.22, 0.23, 0.24, 0.25, 0.36, 0.27, 0.28, 0.29 or 0.3 psi. In certain other aspects, the pressure applied can be 0.001 psi to 100 psi over even higher. The transfilter pressure can be 1 psi, 5 psi, 10 psi, 15 psi, 20 psi, 25 psi, 30 psi, 35 psi, 40 psi, 45 psi, 50 psi, 55 psi, 60 psi, 65 psi, 70 psi, 75 psi, 80 psi, 85 psi, 90 psi, 85 psi, or 100 psi. In one embodiment, the pressure applied to the sample is generated by an electrokinetic, for example, electroosmosis, and a ratchet pump. In yet another embodiment, the pressure is generated using pneumatic or magneto hydrodynamic pumps. In yet a further embodiment, the pressure applied to the fluid is generated by a mechanical device. One example of a useful mechanical pressure generating device is a screw-type pumping device or a peristaltic pump. In a preferred embodiment, the pressure is generated through a compress gas source. Exemplified gases include nitrogen, argon, helium, air, carbon dioxide or oxygen. In certain instances, the pressure is closely related to the total filtration time and sample volume. The lower limit can be even lower than 0.0001 psi as long as the sample can be pumped into the filtration setup. Higher pressure is also possible if high throughput is required. In certain instances, the total filtration time is related to pressure and sample volume. For a large sample volume and low transfilter pressure, a longer total filtration time is expected. For a small sample volume, a shorter time is expected.

The filtration sample can be any body fluid containing tumor cells, or circulating tumor cells. For instance, the sample can be a blood sample from a mammal. In one embodiment, the sample is a peripheral blood sample obtained from a patient.

In some embodiments, the holes have a rectangular shape. The width of the rectangular holes is from 1 to 10 microns, preferably 2 to 8 microns, more preferably 4 to 7.5 microns and even more preferably 5 to 7 microns; and the length of the rectangular holes is from 30 to 50 microns, preferably 35 to 45 microns, more preferably 37 to 42 microns and even more preferably 38.5 to 41.5 microns. In one embodiment of any of the above, the rectangular hole size is 5.5 to 6 by 39.5 to 40 microns. In one instance the rectangular hole size is 5.5 by 40 microns or 6 by 40 microns. In some embodiments, the rectangular holes have a width of 1, 2, 4, 5, 5.5, 6, 6.5, 7, 8, 9 or 10 microns and a length of 30, 31, 32, 33, 34, 35, 36, 37, 38, 39, 40, 41, 42, 43, 44, 45, 46, 47. 48, 50 microns. In other embodiments, the rectangular holes have a minimum width of 1, 2, 4, 5, 5.5, 6, 6.5, 7, 8, 9 or 10 microns and a minimum length of 30, 31, 32, 33, 34, 35, 36, 37, 38, 39, 40, 41, 42, 43, 44, 45, 46, 47. 48, 50 microns. In yet other embodiments, the rectangular holes have a maximum width of 1, 2, 4, 5, 5.5, 6, 6.5, 7, 8, 9 or 10 microns and a maximum length of 30, 31, 32, 33, 34, 35, 36, 37, 38, 39, 40, 41, 42, 43, 44, 45, 46, 47. 48, 50 microns. In some embodiments of any of the above, the sample is passed through the parylene filter under a constant-low-pressure. The pressure can range from 0.01 to 0.5 psi, preferably from 0.05 to 0.4 psi, more preferably from 0.1 to 0.3 psi and even more preferably from 0.1 to 0.25 psi. In one embodiment, the constant pressure is 0.1, 0.11, 0.12, 0.13, 0.14, 0.15, 0.16, 0.17, 0.18, 0.19, 0.2, 0.21, 0.22, 0.23, 0.24 or 0.25 psi. In another embodiment, a maximum constant pressure applied to the sample is 0.1, 0.11, 0.12, 0.13, 0.14, 0.15, 0.16, 0.17, 0.18, 0.19, 0.2, 0.21, 0.22, 0.23, 0.24, 0.25, 0.36, 0.27, 0.28, 0.29 or 0.3 psi.

In some embodiments, a sample is passed through the membrane filter, such as a parylene membrane filter between 1 to 600 seconds. In certain instances, the sample is passed through the parylene membrane filter between 1 to 10 s, 10 to 100 s, 100 to 200 s, 200 to 300 s, 300 to 400 s, 400 to 600s, 100 to 600 s, 100 to 400 s or 50 to 300 s. In some embodiments, passed through the parylene membrane filter for 1, 5, 10, 15, 20, 25, 30, 35, 40, 45, 50, 55, 60, 65, 70, 75, 80, 85, 90, 95, 100, 200, 300, 400, 500, or 600 s.

In yet another aspect, the present invention provides a method for enriching tumor cells, such as CTCs. The method includes passing a sample containing a tumor cell, such as a CTC through a parylene microfilter device comprising a membrane filter consisting of a parylene substrate having an array of holes with a predetermined shape and size; and capturing the circulating tumor cell on the membrane filter, wherein the enrichment of circulating tumor cells is greater than 200, 300, 400, 500, 600, 700, 800, 900, 1000, 1100, 1200, 1300, 1400, 1500, 1600, 1800 or 2000 fold. In one embodiment, the sample is filtered under a constant-low-pressure. In another embodiment, the method provides a greater than 90% capture efficiency and greater than 90% cell viability. In some preferred embodiments, the method provides a greater than 91, 92, 93, 94, 95, 96, 97, 98 or 99% capture efficiency. In other preferred embodiments, the method provides a greater than 91, 92, 93, 94, 95, 96, 97, 98 or 99% cell viability. The sample, the parylene filter, the shape and size of the array of holes and the pressure are as defined in any of the embodiments above. In a preferred embodiment within any of the above embodiments, the holes have a rectangular shape with the dimension as described in any of the above embodiments.

In another aspect, the invention provides a method for isolating a viable tumor cell. The method includes obtaining a sample containing a viable tumor cell; and passing the sample under pressure through a membrane filter consisting of a membrane substrate having a plurality of holes having a predetermined geometric design including predetermined hole shape, dimension and filter opening factor for a time duration sufficient to isolate the viable circulating tumor cell. In one embodiment, the tumor cell is a circulating tumor cell. In another embodiment, the membrane substrate consists of a parylene substrate.

In still another aspect, the present invention provides a system for isolating a live circulating tumor cell. The system includes a parylene microfilter device comprising a membrane filter consisting of a parylene substrate having an array of holes with a predetermined shape and dimension; and a constant pressure delivery system coupled to the parylene microfilter device for maintaining a constant pressure. The sample, the parylene filter, the shape and size of the array of holes and the pressure are as defined in any of the embodiments above. In one embodiment, the pressure is between 0.01 and 0.3 psi such as 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, or 0.3 psi. In a preferred embodiment, the holes have a rectangular shape with the dimension as described in any of the above embodiments. As used herein, a sample containing CTCs is filtered through the membrane filter herein and the solid comprising the CTCs remaining on the filter is called the retentate or filtrand, and the remaining liquid is called the filtrate.

The invention also provides a method of expanding or propagating a filter-captured live cell in culture. The method includes isolating a viable cell, such as a CTC from a sample using a microfilter device under pressure, which comprises a membrane filter consisting of a membrane substrate, such as a parylene substrate having an array of holes with a predetermined dimension and size; and propagating the cell in culture either on filter or by washing them into a culture dish. The conditions for culturing a cell are well known to persons of skill in the art. For example, the cells can be maintained in an incubator at 5% $CO_2$ and 37° C.

In another aspect, the invention provides a 3-dimensional tumor formed in vitro by proliferating a viable circulating tumor cell in culture, wherein the viable circulating tumor cell is isolated by passing a sample containing the tumor cell, such as a CTC through a membrane filter consisting of a parylene substrate under pressure for a time duration sufficient to isolate the viable circulating tumor cell, wherein the parylene substrate has a plurality of holes having a predetermined geometric design.

In another aspect, the invention provides a method for screening the efficacy of an anticancer drug. The method includes isolating a viable circulating tumor cell; contacting the drug with the viable circulating tumor cell; and determining the proliferation activity of the drug contacted viable circulating tumor cell in culture, wherein the viable circulating tumor cell is isolated by passing the sample under pressure through a membrane filter consisting of a parylene substrate having a plurality of holes having a predetermined geometric design for a time duration sufficient to isolate the viable circulating tumor cell. In some embodiments, the anticancer drug is selected from a tyrosine kinase inhibitor or a monoclonal antibody.

Turning now to FIG. 1, a filtration system 100 designed using methods herein is illustrated. FIG. 1A shows a scanning electron micrograph (SEM) 110 of a slot filter having an open-factor of 42%. In certain aspects, to manufacture the membrane filter, parylene-C film is deposited on a silicon wafer. Aluminum is then deposited using a thermal evaporator, followed by lithography and wet-etching patterning. Openings were then etched through parylene-C with an aluminum mask. The patterned parylene membrane filter is peeled off from the silicon substrate. In certain aspects, PDMS sheets are used to sandwich the parylene filter, and form top 127 and bottom 129 fluid chambers (FIG. 1B). The pressure is preferably applied through a pressure delivery system. Those of skill in the art will know of other ways and mechanisms to apply pressure.

FIG. 1B illustrates an embodiment of a filtration system 120 during constant-pressure 125 driven filtration. The sample is introduced above the system, wherein the sample contains CTCs. The sample is filtered through the membrane filter 110 and the solid comprising the CTCs remains on the filter 110 and is called the retentate or filtrand, and the remaining liquid 130 is called the filtrate, which is substantially depleted of CTCs.

A. A Cell Tension Model

Mechanical damage during deformation is one of the most common reasons for cell death. Cells deformation happens in various situations. For instance, during metastasis, CTCs traveling in the bloodstream are forced to deform because of the blood pressure difference, arresting by the microvasculature and interaction with microvessel walls (Weiss et al. *Cell Biophys.*, 1989, 14, 187-215; Weiss, et at *Int. J. Cancer*, 1992, 50, 103-107). Cell membrane expansion usually accompanies with the mechanical deformation, and apparent membrane tension appears and increases during stretching.

It is believed that cell membrane rupture and consequently cell lysis are directly related to the membrane tension (Weiss et al. *Cell Biophys.*, 1989, 14, 187-215; Weiss, et al. *Int. J. Cancer*, 1992, 50, 103-107; Rand, *Biophys. J.*, 1964, 4, 303-316; Kwok, et al. *Biophys. J.*, 1981, 35, 637-652; Taupin, et al. *Biochemistry*, 1975, 14, 4771-4775; Leontiadou, et al. *Biophys. J.*, 2004, 86, 2156-2164; Tomasini, et al. *Exp. Biol. Med.*, 2010, 235, 181-188). In order to estimate the tension during filtration, a simplified cell model is used. A cortical shell-liquid core model, which assumes the membrane is a thin shell and simplifies the internal structure to be a homogeneous liquid drop (Lim, et al. *J. Biomech.*, 2006, 39, 195-216) is used. This model has been extensively used in the analysis of micropipette aspiration, and can correlate the membrane tension with the difference between applied pressure and intracellular pressure (Rand, *Biophys. J.*, 1964, 4, 303-316; Kwok, et al. *Biophys. J*, 1981, 35, 637-652; Lim, et al. *J. Biomech.*, 2006, 39, 195-216).

B. Filtration with a Pore Filter

Most membrane filters, including commercial track-etched filters and micromachined filters, adopt through holes for the size-based capture (Paterlini-Brechot, et al. *Cancer Lett.*, 2007, 253, 180-204; Zheng, et al. *J. Chromatogr., A,* 2007, 1162, 154-161; Vona, et al. *Am. J. Pathol.*, 2000, 156, 57-63; Kahn, et al. *Breast Cancer Res. and Treat,* 2004, 86, 237-247; Zabaglo, et al. *Cytometry A,* 2003, 55, 102-108). In the case of a pore filter (FIG. 2A), the captured cell completely plugs the pore, which is similar to a cell partially aspirated into a micropipette tip. In the micropipette aspiration model, since the suction pressure is usually small, friction between cell membrane and pipette wall are negligible, a uniform tension can be assumed, which means the membrane tension σ of the part deformed into the pore is equal to the tension σ' on the exterior part (Rand, *Biophys. J.,* 1964, 4, 303-316; Kwok, et al. *Biophys. J.,* 1981, 35, 637-652). However, this assumption is less applicable here, because during filtration, the pressure difference $P_c-P_2$ is much smaller than $P_c-P_1$. Reports have shown that for a cell suspended in isotonic solution, the intracellular hydrostatic pressure is only ~2.5 mmH$_2$O (~24.5 Pa) higher than the external surrounding pressure (Kelly, et al. *Am. J. Physiol. Cell Physiol.,* 1991, 260, C652-C657; Rand, et al. *Biophys. J.,* 1964, 4, 115-135). This excess pressure keeps the cell in spherical shape with negligible membrane tension. However, the internal pressure can increase in response to the external applied pressure.

During filtration, since the transfilter pressure (≥0.1 psi (~689 Pa)) is much larger than the original internal pressure, $P_c$ will increase correspondingly and can be approximated by $P_2$, under the assumptions that the volume is near constant, and only a relatively small portion of the cell deformed into the pore (Kelly, et al. *Am. J. Physiol. Cell Physiol.,* 1991, 260, C652-C657; Zydney, et al. *Chem. Eng. Commun.,* 1984, 30, 191-207; W. M. Saltzman, M. S. Thesis, Massachusetts Institute of Technology, 1984). Since there is no fluid flowing through the pore, pressure inside the pore $P_1 \approx 0$. Assuming the leading edge of the membrane deformed into the pore has a semispherical shape, the tension σ using the Laplace's equation can be modeled, $$\Delta P = P_2 - P_1 \approx P_c - P_1 = \frac{2\sigma}{R_p} \quad (4)$$

Hence, $$\sigma = \frac{1}{2} R_p \Delta P \quad (5)$$

where $R_p$ is the pore radius and ΔP is the transfilter pressure drop. The discontinuity of tension across the membrane is balanced by the friction between membrane and filter side walls.

C. Filtration with a Slot Filter

Figure 2B:
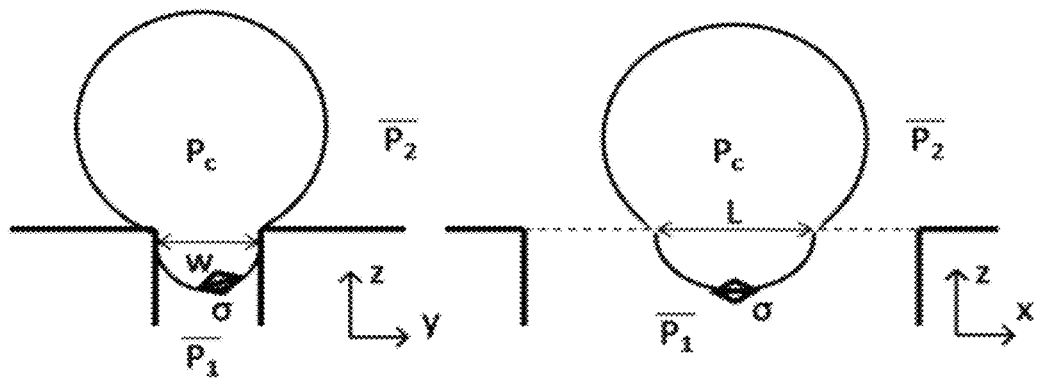

The estimation of tension for cell captured on slot filter is more complicated (FIG. 2B), because the cell is allowed to deform two dimensionally. Under a low transfilter pressure, the exterior part is still near spherical. However, the part deformed into the slot may have lateral deformation. Assume the deformed part is a half-ellipsoid, with three principle axes of L, W and W, where W is the slot width. The internal pressure is assumed to be uniform and can still be approximated by the average exterior pressure $\overline{P_z}$. According to the Laplace's equation, $$\Delta P = \overline{P_2} - \overline{P_1} = Pc - \overline{P_1} = \sigma\left(\frac{1}{R_x} + \frac{1}{R_y}\right) \quad (6)$$

where $R_x$ and $R_y$ are the principle radii of curvature at a point on the ellipsoid surface. Since both the minimum curvature and largest pressure difference appear on the bottom, the maximum tension is also expected there. Assume the deformed part has a length of L in x direction. Then $L_{min}$ should be equal to the slot width, while $L_{max}$ can be approximated to the cell diameter $2 R_0$. The radii of curvature are, $$R_x = \frac{\left(\frac{L}{2}\right)^2}{\frac{W}{2}}, \text{ and } R_y = \frac{W}{2} \quad (7)$$

Hence, $$\Delta P = \sigma\left(\frac{2W}{L^2} + \frac{2}{W}\right) \quad (8)$$

If $W < L < 2 R_0$, $$\frac{1}{4} W \Delta P < \sigma < \frac{1}{2} \Delta P \frac{1}{\frac{W}{4R_0^2} + \frac{1}{W}} \quad (9)$$

Figure 2C:
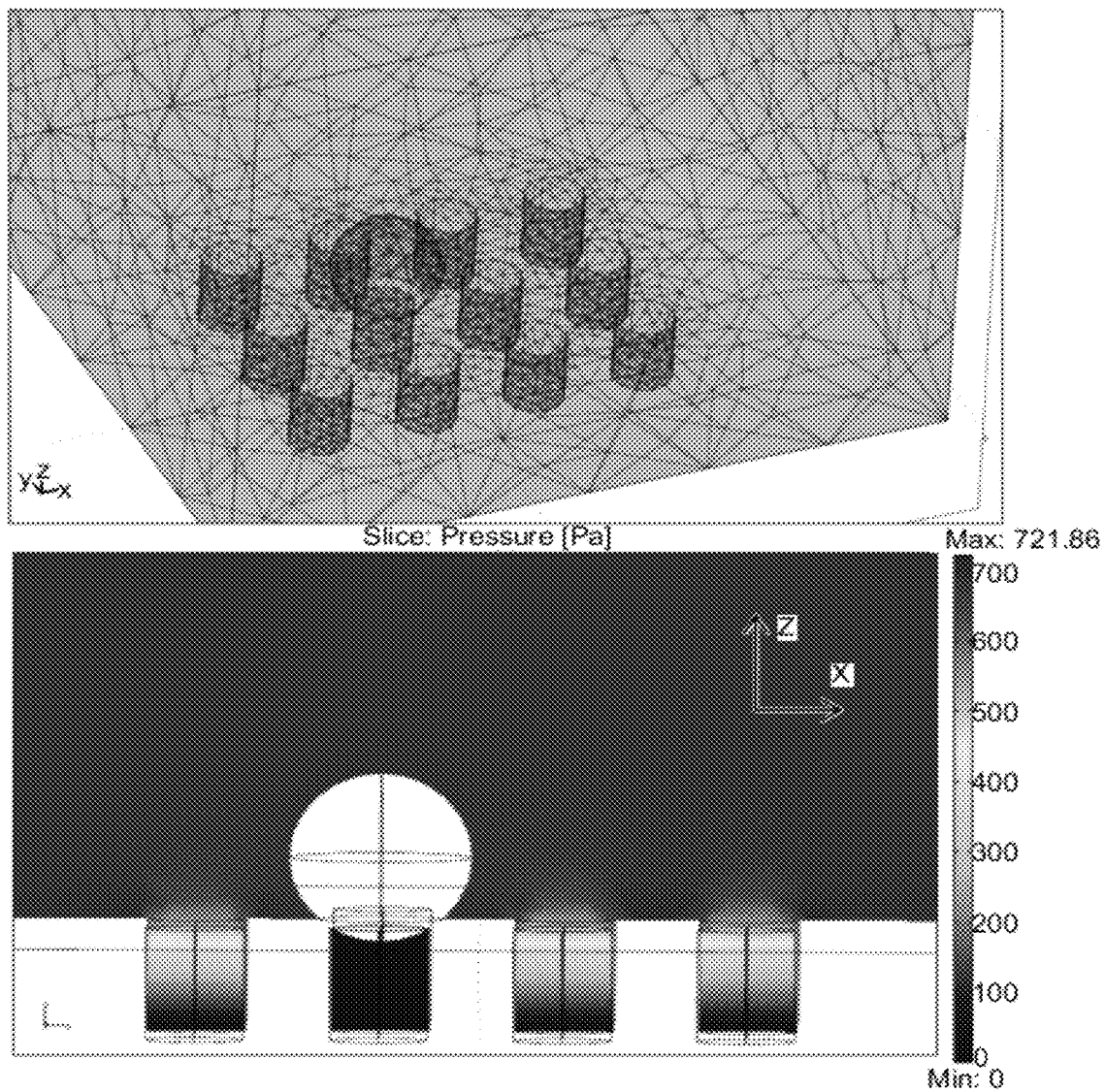
Figure 2D:
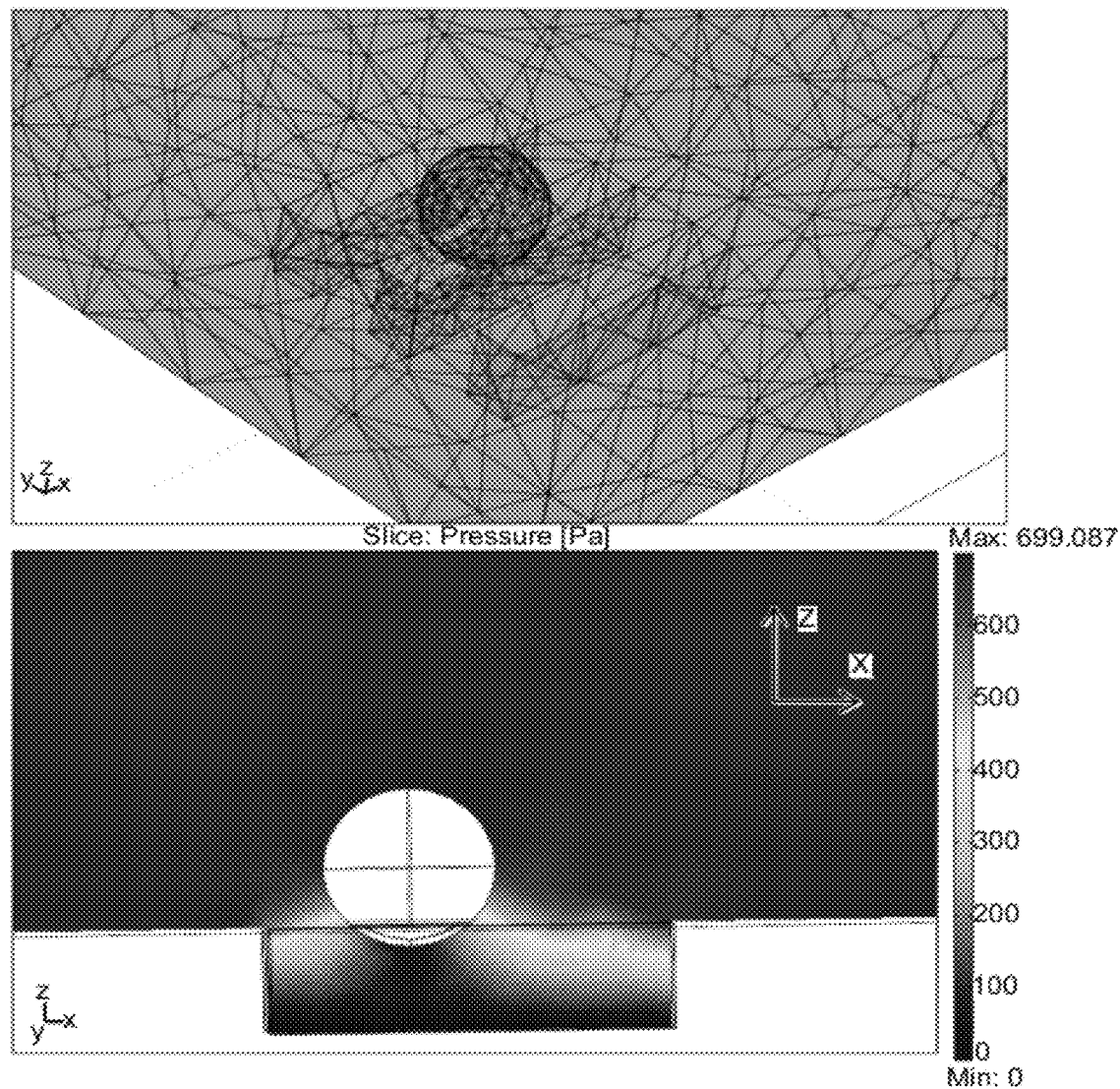

FIG. 2C and FIG. 2D are 3D FEM model of pore and slot filtrations respectively, built by COMSOL Multiphysics.

II. EXAMPLES

A. Methods

Parylene-C was chosen as the filter material because of its good mechanical properties, machinability, biocompatibility and optical transparency in the visible range. The fabrication process of single-layer membrane filters was reported previously. Briefly, it started with a ~10 μm parylene-C film deposition on silicon wafer. Aluminum was then deposited using a thermal evaporator, followed by lithography and wet-etching patterning. Openings were then etched through parylene-C with Aluminum mask, in a 6×6 mm region. Finally, the patterned parylene membrane filter was peeled off from the silicon substrate. PDMS sheets were used to sandwich the parylene filter, and faun top and bottom fluid chambers (FIG. 1B). Two acrylic sheets with central holes were also used. The assembly was clamped to ensure good sealing and prevent leakage. Filtration was carried out through a constant-pressure-driven fluid delivery system, ring filtration, sample was driven into the filter assembly by $N_2$ with low transfilter pressure P.

Non-small-cell prostate cancer PC-3 cells were used for filter device testing and a filtration mechanism study. The PC-3 cell line was cultured in RPMI 1640 culture medium (Mediatech, Inc.) supplemented with 10% fetal bovine serum (RPMI complete medium), maintained at 5% $CO_2$ and 37° C. Upon use, cells were first pre-stained with Calcein-AM, and resuspended in phosphate buffered saline (PBS). Known number of cells were then spiked into either PBS samples, or human whole blood samples from healthy donors. After filtration, capture efficiency (Eq. 1) was measured by counting the captured cancer cells under epifluorescence microscope.

The viability (Eq. 2) of captured cells was evaluated by on-filter staining with Propidium Iodide (PI). Viable cancer cells with intact membrane were able to retain Calcein-AM, thus fluorescing brightly green.

Dead cancer cells with compromised membrane were stained red with PI, while the green fluorescence became faint due to Calcein-AM leakage. Enrichment (Eq. 3) was determined by staining white blood cells (WBCs) remaining on filter with the nucleus dye Acridine Orange (AO) followed by WBC counting.

$$\text{Capture Efficiency} = \frac{\text{\# of captured cancer cells}}{\text{\# of spiked cancer cells}} \quad (1)$$

$$\text{Viability} = \frac{\text{\# of viable cancer cells}}{\text{\# of captured cancer cells}} \quad (2)$$

$$CTC \text{ enrichment (fold)} = \frac{\left[\text{\# cancer} \frac{\text{cells}}{\text{\# WBCs}}\right] \text{ on filter after filtration}}{\left[\text{\# cancer} \frac{\text{cells}}{\text{\# WBCs}}\right] \text{ in original sample}} \quad (3)$$

As one demonstration and application of the high viability of captured CTCs, we also did further cell culture after filtration. About 30 unlabeled PC-3 cells were spiked into 1 mL PBS samples. Samples were filtrated under 0.10 psi transfilter pressure through slot filters with 42% open-factor, and cancer cells were captured on the filter.

Example 1 Illustrates a Comparison of a Pore Filter and a Slot Filter

FIG. 2 illustrates analytical and finite-element models of captured CTCs. FIG. 2A and FIG. 2B are analytical cortical-liquid core models of CTC captured on pore and slot respectively. FIG. 2C and FIG. 2D are 3D FEM model of pore and slot filtrations respectively, built by COMSOL Multiphysics. The pore and slot filters used in FIG. 2C and FIG. 2D have the same open-factor. A transfilter pressure of 0.1 psi is applied as a boundary condition. The simulation results show the pressure distribution around the captured cells. Cell captured by slot is subject to a smaller trans-filter pressure drop order to correlate the transfilter pressure drop ΔP with the transfilter pressure P, 3D fluid models of pore and slot filter filtrations were built by using finite-element simulation tool COMSOL Multiphysics (FIGS. 2C, D). The captured cells were modeled as a solid blocking the flow. Calculated from the postprocessing of pressure distribution, $$\Delta P_{pore} \approx P, \text{ and } \Delta P_{slot} \approx 0.58 \ P \quad (10)$$

The difference between the pore and slot filtrations is expected. Unlike the completely sealed pore, flow can still bypass the cell through the partially plugged slot (slot length>cell diameter). Therefore, for slot filtration, applied pressure is greatly relieved and a much smaller pressure difference on the captured cell is achieved.

Now we make an estimation of the membrane tension if a 0.1 psi transfilter pressure is applied. The optimal filter opening size (i.e., pore diameter or slot width) is determined by CTC capture efficiency and viability, as well as the enrichment. If the opening size is too small, a high CTC viability can be achieved, but too many blood cells will be captured as well, which is undesirable. In previous studies using track-etched polycarbonate pore filters, it was found that the optimal pore filter has the pore diameter of 8 µm (Zabaglo, et al. *Cytometry A*, 2003, 55, 102-108). For slot filter, the optimal slot width is 6 µm (shown in next section). If the cell radius $R_0$=8.5 µm, from Eq. 5, Eq. 9 and Eq. 10, $\sigma_{pore}$=1.3 mN/m, and $\sigma_{slot}$=0.60 mN/m~1.07 mN/m. Therefore, under the same transfilter pressure, slot filter filtration causes a smaller membrane tension and less damage of the captured cell. Compared to the conventional pore filter, slot filter is a better approach for live CTC capture.

B. Parameters of Filtration with Slot Filter

As shown in Eq. 9 and Eq. 10, slot width and transfilter pressure are two parameters for filtration with a slot filter. A cut-off slot width should capture most CTCs, but block as minimal as possible blood cells. A proper pressure is needed to prevent or reduce CTC damage, but allow successful blood sample processing and a good throughput. To experimentally evaluate these two parameters, we spiked the known number of Calcein-AM pre-labeled PC-3 cancer cells into 1 mL whole blood samples. A filter with an open-factor (i.e., the equivalent area of openings/total filter area) of 18% was used in these experiments.

FIG. 3 illustrates filter characterization and properties. Slot filters with open-factor of 18% and 42% were used in experiments. FIG. 3A shows capture efficiency with slot width. FIG. 3B shows viability with slot width. FIG. 3C shows enrichment with slot width. Determined by testing of 18% open-factor filter, 6 µm is the optimal slot width. Filter with 42% had about one-order larger improvement on enrichment. FIG. 3D shows capture efficiency and viability with transfilter pressure. The minimum possible transfilter pressures to process the whole blood sample are 0.13 psi and 0.10 psi for filters with 18% and 42% open-factor, respectively.

Both capture efficiency and viability have the decreasing tendency with increasing slot width (FIGS. 3A, B). A remarkable drop of viability is observed when the slot width increased to 7 µm. This tendency is in accordance with Eq. 9, where the membrane tension increases with slot width. For enrichment, a clear discrepancy appeared between 5 µm and 6 µm slot widths (FIG. 3C). This difference is probably due to some large monocytes (14-17 µm), which may have a threshold passage width between 5 µm and 6 µm. Based on above analysis, filter with 6 µm slot width is optimal since it has over 90% capture efficiency and viability, and allows the passage of most blood cells. Filter performance under different transfilter pressures was also examined (FIG. 3D). As the transfilter pressure increases, both capture efficiency and viability decrease. Hence low transfilter pressure is crucial for live cell capture. Theoretically, the lower transfilter pressure, the higher viability we can achieve. In practice, however, the transfilter pressure is related to the filtration throughput. 0.13 psi was found to be the minimum possible transfilter pressure ensuring high viability and successful blood sample processing for filter with 18% open-factor.

The open-factor is another key parameter. A large open-factor contributes in two aspects to the improved filter performance. Firstly, the large open-factor decreases the flow resistance during filtration. Reduced flow resistance lowers the transfilter pressure required for successful sample processing, which can further reduce the membrane tension, and increase the throughput. The minimum possible transfilter pressure for filter with 42% open-factor is 0.10 psi (FIG. 3D). Secondly, the large open-factor also reduces the filter surface area. Because of their smaller size and larger deformability, most blood cells can deform and pass through the slots during filtration. However, some blood cells may stick to the filter top surface, resulting in a non-ideal CTC enrichment. Reduced filter surface area greatly lowers the chance of blood cell retention on filter surface, thus improving the enrichment. A 42% open-factor could increase the enrichment to 2149-fold (FIG. 3c), one order of magnitude larger than that of 18% open-factor. Further increase in enrichment can be expected for filter with larger open-factor. The drawback, however, is that the filter mechanical strength may be affected if the open-factor is too large.

The constant-pressure-driven fluid delivery method also plays an important role. Most reported filtration approaches used constant-inflow rate-driven sample injection by syringe pump or peristaltic pump, or direct hand-push (see, Paterlini-Brechot, et al. Vona, et al. Kahn, et al. and Zabaglo, et al.). At beginning, a small inflow rate can ensure a low transfilter pressure drop. However, when the slots are gradually plugged by blood cells or other large particles (e.g., macrophages and cell aggregates), although the inflow rate is kept constant, the transfilter pressure drop will increase and may cause damage to captured CTCs. In comparison, constant-pressure-driven strategy can maintain a near-constant transfilter pressure drop.

Example 2 Illustrates a Staining Assay to Determine Live Cancer Cells

In this example, filtration of 1 mL whole blood sample spiked with PC-3 cancer cells took less than 5 min under the minimum possible transfilter pressure. Compared to the low sample processing speed reported for other lateral flow microfluidic based CTC filtration devices (Tan, et al. *Biomed Microdevices*, 2009, 11, 883-892; Kuo, et al. *Lab Chip*, 2010, 10, 837-842; Mohamed, et al. *J. Chromatogr., A*, 2009, 1216, 8289-8295), and microfluidic devices combined with immunoaffinity based selection method (Nagrath, et al. *Nature*, 2007, 450, 1235-1239; Helzer, et al. *Cancer Res.*, 2009, 69, 7860-7866; Gleghorn, et al. *Lab Chip*, 2010, 10, 27-29), we can achieve a much higher throughput. FIG. 4 shows the examples of live and dead cancer cells using Calcein-AM and PI staining assay.

Viable and dead cancer cells can be detected using a calcein-AM and PI staining assays. FIG. 4 shows examples of captured cancer cells and the remaining WBC. FIG. 4A shows that live cancer cells retain Calcein-AM. FIG. 4B shows dead cancer cells are stained with PI, and the pre-labeled Calcein-AM dye leaked out. FIG. 4C shows the remaining WBC were stained with AO. A slot filter with slot size 6×30 µm and 42% open-factor was used here, and the transfilter pressure was 0.1 psi. Due to the large open-factor, few WBCs were left on the filter surface. Most remaining WBCs were stuck inside the slots. (all scale bars: 30 µm).

Example 3 Illustrates the Time-Dependent Viability Drop During Constant-pressure Filtration Due to its high throughput, membrane filters have been shown to be capable of handling samples with large volume (e.g., 7.5 mL) in clinical trials (see, Paterlini-Brechot, et al. Vona, et al. Kahn, et al.; Zabaglo, et al.). However, when high viability is also desirable, more constraints need to be taken into consideration. To examine the capability of processing samples with large volume, Calcein-AM pre-labeled PC-3 cancer cells were spiked into 1-5 mL 1:4 diluted blood samples (e.g., five times diluted blood). Filtration was carried out under different transfilter pressures, ranging from 0.10 psi to 0.20 psi. Total filtration time was recorded for each run. FIG. 5A shows the relations between the viability with total filtration time at different transfilter pressures. For a given transfilter pressure, total filtration time is also a key parameter which greatly influences the viability.

As expected, filtration of samples with larger volume under lower driving pressure took a longer processing time. FIG. 5A shows the time-dependent viability of cancer cells. The time constants of lysis were obtained by fitting the experimental data into Eq. 17. During constant-pressure filtration, although the cell membrane tension can be approximately constant, more and more cells are dead with increasing total filtration time, indicating that the lysis of captured cells is time-dependent. For the same sample volume, although different dilutions (i.e., whole blood, 1:1 diluted blood and 1:4 diluted blood) have different total filtration time, dilutions does not influence the viability of captured cancer cells.

To calculate the membrane tension from the transfilter pressure and Eq. 9, let the slot width W=6 μm, and $R_0$=8.5 μm, $$1.5 \times 10^{-6} \Delta P < \sigma < 2.6 \times 10^{-6} \Delta P \qquad (11)$$

Here we chose the median $\sigma = 2 \times 10^{-6} \Delta P$. According to Eq. 10, $$\sigma = 1.16 \times 10^{-6} P \qquad (12)$$

To analyze the time dependent viability drop, assume the probability of the lysis of captured cancer cells follows the exponential distribution, and the time constant of lysis upon capture is τ, then the cumulative distribution function of a cell which is already dead after it has been captured for a time period of t is:

$$F(t) = 1 - \exp\left(-\frac{t}{\tau}\right) \qquad (13)$$

Correspondingly, the probability of a cell still remaining viable after time t is:

$$P_{viable}(t) = 1 - F(t) = \exp\left(-\frac{t}{\tau}\right) \qquad (14)$$

Assume at time t, the total number of captured cancer cells is N, and the spiked cancer cells are uniformly distributed in the sample, then the time interval between two capture events is:

$$\Delta t = \frac{t}{N} \qquad (15)$$

Then at time t, the expectation of the viability of captured cells is:

$$V(t) = \frac{1}{N} \sum_{n=1}^{N} \exp\left(-\frac{1}{\tau} \frac{n}{N} t\right) = \frac{\Delta t}{t} \sum_{n=1}^{N} \exp\left(-\frac{n \Delta t}{\tau}\right) \qquad (16)$$

If N is large (i.e., $\Delta t \to 0$ for a finite t), $$V(t) = \frac{1}{t} \int_0^t \exp\left(-\frac{t'}{\tau}\right) dt' = \frac{\tau}{t\left(1 - \exp\left(-\frac{t}{\tau}\right)\right)} \qquad (17)$$

The cell lysis time constants were obtained by fitting experimental data into Eq. 17 (FIG. 5A). As expected, smaller time constant is observed for high pressure filtration, indicating faster lysis and lower viability of captured cancer cells. In certain instances, the present invention provides the use of a statistical approach to correlate the viability of cells to the total filtration time and transfilter pressure. In a preferred aspect, cell viability is directly related to the total filtration time, and the time constant a is a bridge to connect the viability to the transfilter pressure.

Example 4 Illustrates the Discovery of the Safe Golden Zone

A. Molecular Model of Membrane Rupture

In previous literature studying the lysis of red blood cells during micropipette aspiration or membrane filtration, time-related cell lysis was observed, and this phenomenon was explained by the viscoelasticity of cell membrane under constant tension (R. P. Rand, Biophys. J., 1964, 4, 303-316). It was found that the cell membrane will be ruptured if the strain on the cell membrane resulted from the deformation exceeds the critical strain for lysis. The strain in the membrane, at a given tension, is a function of time, which behaves like a viscoelastic material. However, the viscoelastic model itself may not be able to fully depict the underlying physical mechanism of the time-dependent viability drop, since no molecular structures are represented by the springs and dashpots. For instance, in Rand's model, in the latter stage, the strain increases linearly with time. However, for traditional viscoelastic materials, the strain rate usually decreases with time. This discrepancy between cell membrane and other viscoelastic materials may be resulted from its special structure.

From the molecular view, it is believed that under mechanical stress or tension, meta-stable nanosized pores appear in the lipid membrane, and the expansion of the pores beyond a critical radius leads to the irreversible membrane breakdown (Taupin, et al. Biochemistry, 1975, 14, 4771-4775; Leontiadou, et al. Biophys. J., 2004, 86, 2156-2164; Tomasini, et al. Exp. Biol. Med., 2010, 235, 181-188). The membrane's resistance to rupture is represented in term of a line tension γ. The free energy E of the formation of a pore with radius R is:

$$E(R, \sigma) = 2\pi R \gamma - \pi R^2 \sigma \qquad (18)$$

where the first term on the right is the edge energy of the pore and the second term represents the work of the tension σ. E(R) reaches its maximum, $$E(R^*) = E^* = \frac{\pi \gamma^2}{\sigma}, \text{ when } R = R^* = \frac{\gamma}{\sigma}.$$

Therefore, when R<R*, the pores tend to reseal, while when R>R*, the pore tends to grow rapidly and lead to the membrane breakdown. The typical critical radius for the formation of pores is 0.3~0.5 nm. In our work, we take into consideration of one more energy term (C) corresponding to the energy of exposing intracellular materials outside when nanopores exist and the loss of intracellular materials starts. Therefore, the modified energy balance is:

$$E(R, \sigma) = 2\pi R\gamma - \pi R^2(\sigma + C) \quad (19)$$

If assuming the energy of pores has Boltzmann distribution, and the probability of the rupture of cells follows the exponential distribution, there is a relation between the time constant $\tau$ of cell lysis and the membrane tension $\sigma$, $$\text{Log}\tau = A + \frac{E^*(\sigma)}{k_B T} = A + \frac{\pi\gamma^2}{k_B T}\frac{1}{(\sigma + C)} \quad (20)$$

where $k_B$ is the Boltzmann constant, T is the absolute temperature and A is a constant.

FIG. 6 shows the fitting of time constants with tensions using Eq. 20. The line tension is $\gamma = 0.75 \times 10^{-11}$ N, which is very close to the reported value $1 \times 10^{-11}$ N for lipid bilayer. The energy term of exposing intracellular material outside is determined to be $$C = \frac{0.00243 \text{ N}}{\text{m}}.$$

FIG. 6 shows the relationship between Log($\tau$) and tension according to (a) the molecular model, and (b) the Griffith's failure model, respectively. Experimental data are fitted into Eq. 20 and Eq. 28, respectively.

B. Griffith's Failure Model of Membrane Rupture

From another point of view, the appearance of nanosized pores and the rupture of cell membrane under tension can also be explained by the Griffith's failure theory. Although Griffith's failure theory is mainly used to study the failure of brittle materials from an atomic view in fracture mechanics (T. L. Anderson, Fracture mechanics: fundamentals and applications, CRC Taylor & Francis Group, Boca Raton, Fla., 3$^{rd}$ edn., 2005, ch. 2, 25-30), it also applies to cell membrane since membrane can be considered to constitute of lipid molecules. Potential energy exists as a function of lipid molecular separation. At the equilibrium distance, the potential energy has the minimum value, and the attractive and repelling forces are balanced (see Anderson). According to the Griffith's theory, a pore can form (or an existing pore can grow) only if this process decreases or remains the total energy, as shown in Eq. 21.

$$\frac{dE_{total}}{dr} = \frac{dU}{dr} + \frac{dW}{dr} = 0 \quad (21)$$

where r is the pore radius, U is the work done by the tension and W is the edge energy. Assuming E is the Young's modulus, $\gamma$ is the line tension, b is the membrane thickness, and C is the energy term from exposing intracellular material outside, then $$U = -\frac{\pi s F^2 r^2 b}{E} - C\pi r^2 \quad (22)$$

$$\frac{dU}{dr} = -\left(\frac{F^2 b}{E} + C\right)2\pi r = -\left(\frac{\sigma^2}{Eb} + C\right)2\pi r \quad (23)$$

Here F is the stress, and $$F = \frac{\sigma}{b},$$

where $\sigma$ is the membrane tension.

$$W = 2\pi r\gamma \quad (24)$$

$$\frac{dW}{dr} = 2\pi\gamma \quad (25)$$

According to Eq. 21, $$\frac{dU}{dr} = -\frac{dW}{dr}, \text{ and } r^* = \frac{\gamma}{\frac{\sigma^2}{Eb} + C} \quad (26)$$

when $r = r^*$, $$E_{total} = 2\pi\gamma r^* - \left(\frac{\sigma^2}{Eb} + C\right)\pi r^{*2} = \frac{\pi\gamma^2}{\frac{\sigma^2}{Eb} + C} \quad (27)$$

According to Taupin, et al. *Biochemistry*, 1975, 14, 4771-4775.

$$\text{Log}\tau = A + \frac{\pi\gamma^2}{\left(\frac{\sigma^2}{Eb} + C\right)kT} \quad (28)$$

where A is a constant.

From the literature, we choose the Young's modulus to be $1 \times 10^6$ Pa, and the thickness to be about 4 nm (R. P. Rand, *Biophys. J.*, 1964, 4, 303-316; J. C. Weaver, *Ann. NY Acad. Sci.*, 1994, 720, 141-152). By fitting the experimental data of the relation between Log($\tau$) and $\sigma^2$ into Eq. 28, the line tension is found to be $\gamma = 0.57 \times 10^{-11}$ N, and the energy term of exposing intracellular material is $$C = \frac{0.00172 \text{ N}}{\text{m}},$$

which are in good agreement with the previous molecular model.

It is worth mentioning that many reports have shown that nucleated cells are able to repair their plasma membranes to reseal membrane wounding and protect themselves from rupture (McNeil, et al. *Annu. Rev. Cell Dev. Biol.*, 2003, 19, 697-731). However, if a membrane tension is artificially imposed, the resealing can be slowed down (McNeil, et al. *Annu. Rev. Cell Dev. Biol.*, 2003, 19, 697-731; Zhelev, et al. *Biochim. Biophys. Acta*, 1993, 1147, 89-104). At high tensions, this resealing can even be completely blocked. In this work we do not take into consideration the membrane repairmen, which may be reasonable since artificial tension is exerted by capture and pressure drop.

C. The Discovery of the Safe Golden Zone

Figure 7A:
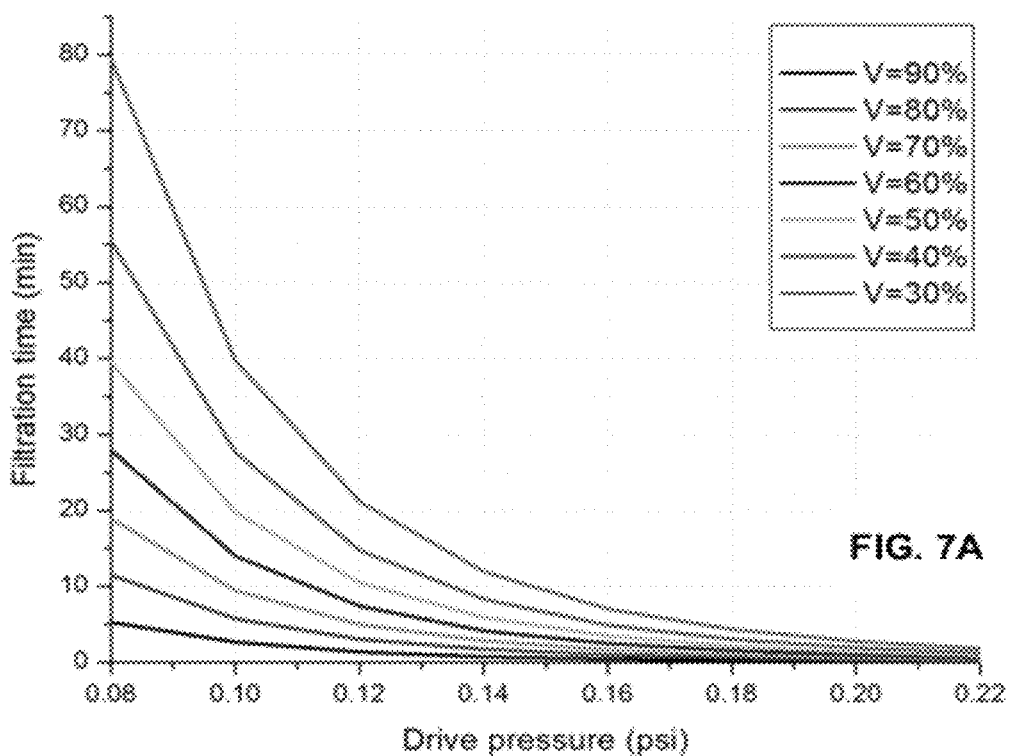
FIGS. 7A-B illustrate the safe "golden zone" regarding the transfilter pressure and total filtration time, according to (a) the molecular model (combining Eq. 12, Eq. 17 and Eq. 20), and (b) the Griffith's failure model (combining Eq. 12, Eq. 17 and Eq. 28). Operation below a contour with viability of V can achieve a viability higher than V.
Figure 7B:
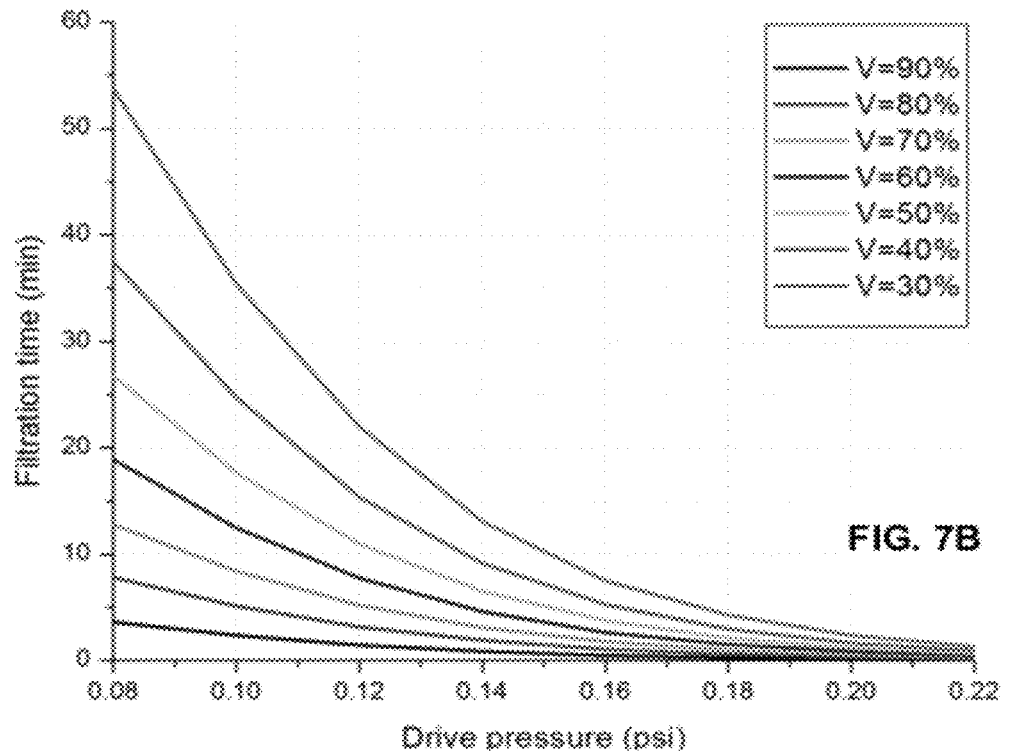

From the molecular model and the Griffith's models discussed above, a "golden zone" regarding the transfilter pressure and total filtration time was discovered. According to Eq. 12, Eq. 17, Eq. 20 and Eq. 28, cell viability with transfilter pressure and total filtration time was correlated. Therefore, for a given viability, the transfilter pressure and total filtration time place restrictions on each other. FIG. 7 shows that both models (FIG. 7A, the molecular model; FIG. 7B, the Griffith's failure mode) predict similar safe zones. Operation below a contour with viability of V can achieve a viability higher than V. These viability contours plots can aid in filtration design to tailor the proper transfilter pressure and/or the maximum sample volume for viable CTC capture.

FIG. 7 illustrates the safe "golden zone" regarding the transfilter pressure and total filtration time, according to (FIG. 7A) the molecular model (combining Eq. 12, Eq. 17 and Eq. 20), and (FIG. 7B) the Griffith's failure model (combining Eq. 12, Eq. 17 and Eq. 28). Operation below a contour with viability of V can achieve a viability higher than V.

In order to process samples of large volume with high CTC viability, an increase in the effective membrane filter area reduces the total filtration time. In certain embodiments herein, the total effective filtration area is 6×6 mm, which can be easily increased to 8×8 mm, 10×10 mm, 12×12 mm, 14×14 mm, 16×16 mm, 18×18 mm, 20×20 mm, 22×22 mm, 24×24 mm, 26×26 mm, 28×28 mm, 30×30 mm, 32×32 mm, 34×34 mm, 36×36 mm, 38×38 mm or 40×40 mm.

In other embodiments, a jig design with multiple chambers, which enables parallel filtration through multiple filters in an array is also within the ambit of the present invention.

The present invention provides in part, membrane filter design methods to maximize efficiencies of viable CTC capture from human samples (e.g., blood), as well as the important parameters of filter design and filtration conditions. In certain aspects for viable cell capture, a slot filter is found to be a better than a pore filter, because CTCs captured by slot suffer from less membrane tension. In other aspects, a larger open-factor can achieve higher throughput and enrichment. In still other aspects, compared to the constant-inflow rate-driven method, the constant-pressure-driven fluid delivery aids in maintaining a low transfilter pressure drop during filtration. Low transfilter pressure plays a critical role in preserving high CTC viability. For a given viability, the maximum total filtration time or sample volume is restricted by the transfilter pressure. Operating in the safe "golden zone" regarding the transfilter pressure and total filtration time can ensure high CTC viability.

Example 5 Illustrates a 3D Cell Culture

For 2D cell culture, filter with captured cells was first disassembled from the jig, and then soaked in RPMI complete medium and placed in an incubator. For 3D cell culture, Matrigel was selected as the 3D scaffold material. A 1:1 mixture of Matrigel (BD Biosciences) and RPMI complete medium was carefully injected into the filter top chamber by a syringe pump, to prevent the cell damage and undesirable bubble appearance. Gelation was allowed to occur at 37° C. for 30 min. Then the filter assembly was placed inverted and covered with RPMI complete medium. The whole setup was left in a Petri-dish and placed in an incubator. Culture medium was refreshed every day.

Figure 8A:
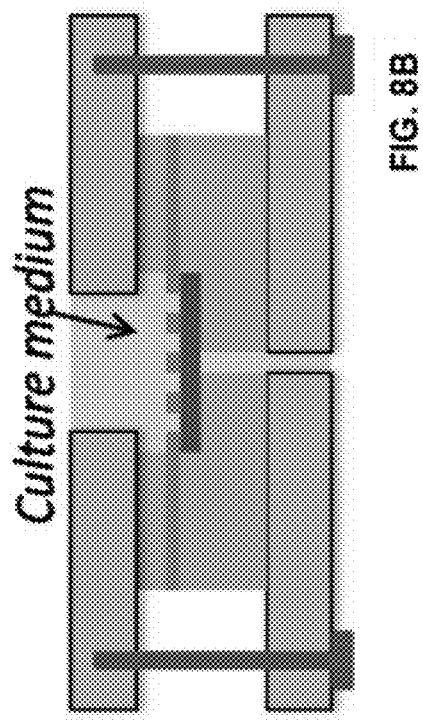
FIGS. 8A-B illustrate 3D culture operation procedures. (A) Inject Matrigel into filter chamber by syringe pump after filtration. (B) Place the filter assembly inverted, and soak in culture medium.
Figure 8B:
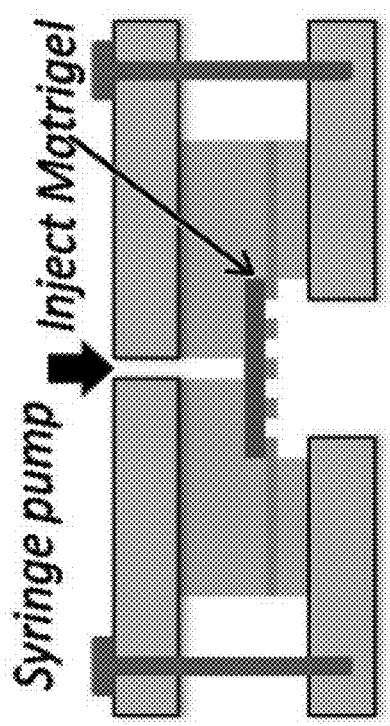

Turing now to FIG. 8, a 3 dimensional (3D) cell culture operation procedure is illustrated. In FIG. 8A, a gelatinous protein mixture such as Matrigel is injected into a filter chamber by a syringe pump after filtration of a sample containing CTCs. Thereafter, the filter assembly is inverted and soak in culture medium (See, FIG. 8B). In certain instance, the CTCs are mechanically captured on the slots of the filter, and as matrigel has been injected into the chamber before inversion, the CTCs stay in place.

To demonstrate the feasibility of on-filter 3D culture of the captured cancer cells after filtration, we spiked about 30 unlabeled PC-3 cancer cells into 1 mL PBS. The sample was filtrated and cancer cells were captured on the filter. Matrigel was selected as the 3D scaffold material. A 1:1 mixture of Matrigel (BD Biosciences) and RPMI complete medium was carefully injected into the filter top chamber by a syringe pump, to prevent the cell damage and undesirable bubble appearance. Gelation was allowed to occur at 37° C. for 30 min. Thereafter, the filter assembly was placed invertedly and covered with RPMI complete medium. The whole setup was left in a Petri-dish and placed in an incubator. Culture medium was refreshed every day. Calcein-AM and PI live/dead cell staining was used again to determine the cellular viability of the 3D tumor. 2D monolayer cancer cell culture without Matrigel injection was used as a control. For 2D on-filter culture, membrane filter was disassembled after filtration and soaked in the culture medium.

Immunofluorescence staining was performed on the 2D monolayer cultures and 3D tumors after 8 days of culture. FITC-conjugated anti-EpCAM antibody (BioLegend) and PE-conjugated anti-CD49b antibody (BD Biosciences) were used to immunostain the cancer cell membranes. After staining, images were taken by a Nikon E800 epifluorescence microscope (Nikon Inc.), equipped with a CCD camera.

FIG. 9A illustrates one aspect of a 3D on-filter cultured tumor growth rate and cell viability. As expected, as the culture time increases, so does the number of cells in the tumor in an exponential fashion. FIG. 9B illustrates the viability on the $6^{th}$ day of culture. FIG. 9C-9E show bright field and fluorescence images of calcein-AM & PI stained tumor. All scale bars: 40 μm.

For on-chip 3D cell culture, cell-cell and cell-extracellular matrix (ECM) interactions dominate over cell-substrate interaction. Therefore, we needed to treat the filter surface to be resistant to cancer cell adhesion. Surface property and cancer cell adhesion evaluations of untreated parylene-C, $O_2$ plasma treated parylene-C, parylene-C with parylene-HT coating, and polystyrene was evaluated. Untreated parylene-C surface was hydrophobic. While plasma treatment could turn it to be hydrophilic, parylene-HT coating rendered the surface to be even more hydrophobic. After 10 hours of incubation, about 30% PC-3 cancer cells remained adhering on the untreated parylene-C surface. Untreated parylene-C surface could be considered as cell resistant compared to the tissue culture polystyrene control. During 3D tumor culture, some cancer cells adhered and proliferated two-dimensionally on the untreated parylene-C filter. It was noticed that plasma treated parylene-C surface displayed enhanced adhesion. In comparison, parylene-HT coated surface heavily repelled cancer cell adhesion, reducing the cell adhesiveness to be only one-third of the original level.

Therefore, parylene-HT coated parylene-C filter was selected for 3D culture after filtration. Captured PC-3 cancer cells proliferated three-dimensionally into the Matrigel, and gradually formed a spherical tumor. Matrigel is a biomatrix hydrogel containing many essential components of the ECM such as collagen, laminin, entactin and other important growth factors, which can support cellular proliferation and induce cellular differentiation. The cellular proliferation rate was monitored. On the 6$^{th}$ day, live/dead staining was used to evaluate the cellular viability inside the tumor. Over 90% cells kept viable during the tumor formation. To further investigate the structure of the tumor, after 8 days of culture, we stained the cell membranes with cancer specific immunofluorescence surface markers. The images indicated that separate cells were adhering to form a combined structure. Cell-cell and cell-ECM interactions were clearly observed. In comparison, 2D on-filter culture was used as a control. Cells attached to parylene-C filter, and formed a confluent 2D monolayer after 8 days of culture.

Figures 10A, 10B:
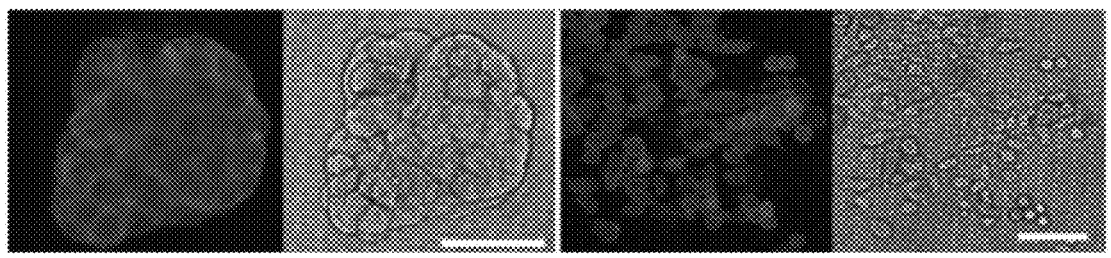
FIGS. 10A-D illustrates immuno-staining of cultured 3D tumor (with parylene-HT coated parylene filter) and 2D monolayer cells (on untreated parylene-C filter). (A)&(B) 3D tumor and 2D monolayer cells stained with FITC-conjugated anti-EpCAM antibody. (C)&(D) 3D tumor and 2D monolayer cells stained with PE-conjugated anti-human CD49b antibody. (all scale bars: 100 μm).
Figures 10C, 10D:
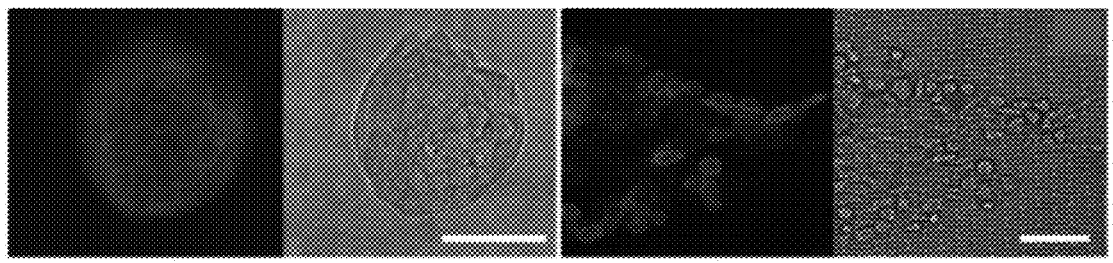

FIG. 10 illustrates immuno-staining of (A) a cultured 3D tumor with parylene-HT coated parylene filter and 2D monolayer cells on untreated parylene-C filter. FIG. 10A shows a 3D tumor and FIG. 10B shows 2D monolayer cells stained with FITC-conjugated anti-EpCAM antibody. FIG. 10C shows 3D tumor and FIG. 10D shows 2D monolayer cells stained with PE-conjugated anti-human CD49b antibody. (all scale bars: 100 μm).

FIG. 11 shows the surface property and cancer cell adhesion evaluations of (1) untreated parylene-C; (2) $O_2$ plasma treated parylene-C, (3) parylene-C with parylene-HT coating, and (4) polystyrene are shown in (see, FIG. 11A-B). FIG. 11C shows that during 3D tumor culture, some cancer cells adhered and proliferated two-dimensionally on the untreated parylene-C filter.

In certain aspects, the large open-factor contributed in two aspects to the improved filter performance. First, the large open-factor decreased the flow resistance during filtration. Reduced flow resistance lowered the transfilter pressure required for successful sample processing and the trans-filter pressure drop ΔP, which ensured the high viability of captured cancer cells. Filter testing with the model system showed that the capture efficiency was 92.4% (SD=7.4%), and the viability was measured to be 93.8% (SD=3.4%).

Second, the large open-factor also decreased the filter surface area. Because of their smaller size and larger deformability, most blood cells can deform and pass through the slots during filtration. However, some blood cells may remain on the filter top surface, resulting in a non-ideal CTC enrichment. Reduced filter surface area greatly lowers the chance of blood cell retention on filter surface, thus improving the enrichment. The filter (open-factor 42%) achieved a 2149-fold (SD=1120) enrichment.

This example shows the advantages of the use of a high open-factor parylene-C/HT filter for the capture of CTCs from whole blood, with high capture efficiency, viability, enrichment and throughput. Due to the large open-factor, CTC enrichment was much higher than previous filters. Moreover, for the first time, the feasibility of 3D tumor culture was demonstrated after filtration. Captured cancer cells were cultured on-filter, and proliferated into Matrigel three-dimensionally. Live/dead staining assay and immunofluorescence staining verified the cellular viability and the morphology of the 3D tumor.

Example 6 Illustrates a Filter Design

This example shows the advantages of the using the present invention to design a filter system for capturing viable tumor cells at high efficiency and high viability. In this example, a parylene membrane is used with rectangular holes. In this example, an isolated cell has a viability of greater than 90%. The plurality of holes have a dimension of 6 μm by 40 μm and the pressure is between 0.01 psi and 0.2 psi. The area opening ratio or factor is 18%. A pressure source is coupled to the filter for applying pressure to a sample and there is a substantially constant transfilter pressure drop.

The hole shape, the filter opening factor or area, the transfilter pressure and the total filtration time is balanced, tailored or optimized in order to achieve greater than 90% viability of the tumor cells, in accordance with equations (I) and (II):

$$V(t) = \frac{\tau}{t}\left(1 - \exp\left(-\frac{t}{\tau}\right)\right) \quad (I)$$

$$\text{Log}\tau = A + \frac{E^*(\sigma)}{k_B T} = A + \frac{\pi\gamma^2}{k_B T}\frac{1}{(\sigma + C)} \quad (II)$$

V(t) is accumulative viability is greater than 90%. In this example, the value for t is about 4 minutes. The value for τ, which is the time constant of lysis upon capture is 10.66 minutes. E* is the free energy of the formation of a single hole and has a value of is 0.04329 $k_B T$. The temperature is 278°K. σ is tension and has a value of 0.0008 N/m with a transfilter pressure of 0.1 psi. γ is a line tension and has a value of 0.75×10$^{-11}$ N. C is 0.00243N/m; and A is −6.70 in the molecular membrane model or −6.72 in the Griffith's model.

A skilled artisan will appreciate that it is possible to start with a filter area and a filter opening factor, then Equation I and II then allow the calculation of the viability. If the viability is not satisfactory, one can increase the filter area and/or the filter opening factor, and then recalculate the viability. One can then quickly reach the right numbers for the viability to be achieved.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for isolating a viable tumor cell, said method comprising:
   obtaining a sample containing a viable tumor cell; and
   passing the sample under pressure through a membrane filter consisting of a membrane substrate having a plurality of holes having a predetermined geometric design including predetermined hole shape, dimension and filter opening factor for a time duration, said membrane filter designed by
   providing a membrane filter consisting of a membrane substrate having a plurality of holes having a predetermined geometric design, the geometric design includes predetermined hole shape, dimension and filter opening factor;
   providing a pressure source coupled to the filter for applying pressure to a sample, wherein the transfilter pressure applied to the sample is 0.05 to 0.23 psi;
   maintaining a substantially constant transfilter pressure drop;
   choosing the hole shape, filter opening factor, transfilter pressure and total filtration time in accordance with equations (I) and (II):

$$V(t) = \frac{\tau}{t}\left(1 - \exp\left(-\frac{t}{\tau}\right)\right) \quad (I)$$

$$\text{Log}\tau = A + \frac{E^*(\sigma)}{k_B T} = A + \frac{\pi\gamma^2}{k_B T}\frac{1}{(\sigma + C)} \quad (II)$$

wherein:
V(t) is the accumulative viability of captured cells;
t is total filtration time
τ is the time constant of lysis upon capture;
E* is the free energy of the formation of a single hole;
σ is tension;
$k_B$ is the Boltzmann constant;
T is the absolute temperature;
γ is a line tension;
C is an energy term; and
A is a constant, to thereby obtain filtered cells between 70% to about 99.0% viable.

2. The method of claim 1, wherein the tumor cell is a circulating tumor cell.

3. The method of claim 1, wherein the membrane substrate is a parylene substrate.

4. The method of claim 1, wherein the isolated cell has a viability of greater than 90%.

5. The method of claim 1, wherein the plurality of holes has a rectangular shape.

6. The method of claim 5, wherein the plurality of holes has a dimension of 6 μm by 40 μm.

7. The method of claim 1, wherein the pressure is between 0.11 psi and 0.2 psi.

8. The method of claim 1, wherein the sample is passed through the parylene membrane filter between 1 second to 30 minutes.

9. The method of claim 8, wherein the sample is passed through the parylene membrane filter between 100 seconds to 600 seconds.

10. The method of claim 4, wherein the membrane filter has an opening-factor between 95% and 99%.

11. The method of claim 1, wherein transfilter pressure is a member selected from the group consisting of 0.11, 0.12, 0.13, 0.14, 0.15, 0.16, 0.17, 0.18, 0.19, 0.2, 0.21, 0.22, and 0.23 psi.

12. The method of claim 1, wherein transfilter pressure is 0.1 to 0.2 psi.

13. The method of claim 1, wherein:
t is about 1 second to about 60 minutes;
τ is about 1 second to about 60 minutes;
E* is the free energy of the formation of a single hole and is 0.04329 $k_B$T for the molecular membrane model and is 0.02485 $k_B$T for the Griffith's model;
σ is about 0.0008 N/m to about 1.0 N/m for the molecular membrane model and about 0.0000005 $N^2/m^2$ to about 1.0 $N^2/m^2$ for the Griffith's model;
$k_B$ is equal to $1.3806504 \times 10^{-23}$ $JK^{-1}$;
T is between 273°K to about 310°K
γ is between $1 \times 10^{-8}$ to about $1 \times 10^{-12}$;
C is 0.00243N/m; and
A is −6.70 in the molecular membrane model or −6.72 in the Griffith's model.

14. The method of claim 1, wherein said cells are members selected from the group consisting of animal cells and plant cells.

15. The method of claim 14, wherein said cells are animal cells.

16. The method of claim 1, wherein said cells are members selected from the group consisting of fetal cells, white blood cells, red blood cells, epithelial cells circulating tumor cells, tissue tumor cells and a combination thereof.

17. The method of claim 1, wherein said membrane substrate is a member selected from the group consisting of a polymer and parylene.

18. The method of claim 17, wherein said membrane substrate is parylene.

* * * * *